(12) United States Patent
Turner et al.

(10) Patent No.: US 8,170,643 B2
(45) Date of Patent: May 1, 2012

(54) SYSTEM AND METHOD FOR IRRADIATING A TARGET WITH ELECTROMAGNETIC RADIATION TO PRODUCE A HEATED REGION

(75) Inventors: Paul F. Turner, Bountiful, UT (US); Mark Hagmann, Salt Lake City, UT (US)

(73) Assignee: BSD Medical Corporation, Salt Lake City, UT (US)

( * ) Notice: Subject to any disclaimer, the term of this patent is extended or adjusted under 35 U.S.C. 154(b) by 1011 days.

(21) Appl. No.: 12/154,808

(22) Filed: May 23, 2008

(65) Prior Publication Data
US 2008/0228063 A1    Sep. 18, 2008

Related U.S. Application Data

(63) Continuation-in-part of application No. 11/286,104, filed on Nov. 22, 2005, now Pat. No. 7,565,207.

(51) Int. Cl.
*A61B 5/05* (2006.01)
*A61N 5/00* (2006.01)

(52) U.S. Cl. .................. 600/411; 607/101; 607/156

(58) Field of Classification Search .......... 607/100–102, 607/154, 156; 600/407, 408, 410, 423; 324/306–309, 318, 322
See application file for complete search history.

(56) References Cited

U.S. PATENT DOCUMENTS

| | | | |
|---|---|---|---|
| 2,533,900 A | 12/1950 | Shanklin | |
| 3,095,880 A | 7/1963 | Haagensen | |
| 3,594,802 A | 7/1971 | Koob | |
| 4,397,313 A | 8/1983 | Vaguine | |
| 4,434,341 A | 2/1984 | Busby | |
| 4,462,412 A | 7/1984 | Turner | |
| 4,554,925 A | 11/1985 | Young | |
| 4,586,516 A | 5/1986 | Turner | |
| 4,589,423 A | 5/1986 | Turner | |
| 4,612,940 A | 9/1986 | Kasevich et al. | |
| 4,633,875 A | 1/1987 | Turner | |
| 4,638,813 A | 1/1987 | Turner | |
| 4,672,980 A | 6/1987 | Turner | |
| 4,798,215 A | 1/1989 | Turner | |
| 4,869,247 A | 9/1989 | Howard, III et al. | |
| 4,881,034 A * | 11/1989 | Kaufman et al. | 324/318 |
| 5,097,844 A * | 3/1992 | Turner | 607/156 |
| 5,101,836 A | 4/1992 | Lee | |

(Continued)

FOREIGN PATENT DOCUMENTS

DE    2420883    11/1975

(Continued)

*Primary Examiner* — Tse Chen
*Assistant Examiner* — Patricia Park
(74) *Attorney, Agent, or Firm* — Thorpe North & Western LLP

(57) ABSTRACT

A system and corresponding method for irradiating a target with electromagnetic radiation to produce a heated region. The system comprises a coupling device operable to couple electromagnetic radiation from a magnetic resonance imaging system. A plurality of energy radiator applicators are connected to the coupling device to receive electromagnetic radiation energy from the coupling device. Each of the radiator applicators is operable to emit a radio frequency heating signal using the electromagnetic radiation energy from the coupling device. A bolus filled with a dielectric fluid is positioned within the inner area of the MRI system. The bolus is operable to receive the radio frequency heating signals from the plurality of energy radiator applicators and direct the radio frequency heating signals into a section of the body to produce a heated region within the body.

27 Claims, 13 Drawing Sheets

U.S. PATENT DOCUMENTS

| | | | |
|---|---|---|---|
| 5,109,853 A | 5/1992 | Taicher et al. | |
| 5,184,076 A * | 2/1993 | Ehnholm | 324/318 |
| 5,251,645 A | 10/1993 | Fenn | |
| 5,284,144 A * | 2/1994 | Delannoy et al. | 600/412 |
| 5,441,532 A | 8/1995 | Fenn | |
| 5,492,122 A | 2/1996 | Button et al. | |
| 5,501,655 A | 3/1996 | Tolt et al. | |
| 5,540,737 A | 7/1996 | Fenn | |
| 5,810,888 A | 9/1998 | Fenn | |
| 5,895,356 A | 4/1999 | Andrus et al. | |
| 6,087,832 A * | 7/2000 | Doty | 324/318 |
| 6,200,598 B1 | 3/2001 | Needham | |
| 6,208,903 B1 * | 3/2001 | Richards et al. | 607/101 |
| 6,304,769 B1 | 10/2001 | Arenson et al. | |
| 6,470,217 B1 | 10/2002 | Fenn et al. | |
| 6,567,684 B1 | 5/2003 | Chenevert et al. | |
| 6,592,847 B1 | 7/2003 | Weissleder et al. | |
| 6,807,446 B2 * | 10/2004 | Fenn et al. | 607/101 |
| 6,827,926 B2 | 12/2004 | Robinson et al. | |
| 6,904,323 B2 | 6/2005 | Samulski | |
| 6,917,338 B2 | 7/2005 | Bergervoet et al. | |
| 7,087,026 B2 | 8/2006 | Callister et al. | |
| 7,123,010 B2 | 10/2006 | Krockel | |
| 7,227,360 B2 * | 6/2007 | Jevtic et al. | 324/318 |
| 2002/0193849 A1 | 12/2002 | Fenn et al. | |
| 2003/0004454 A1 | 1/2003 | Fenn et al. | |
| 2005/0251234 A1 * | 11/2005 | Kanzius et al. | 607/101 |

FOREIGN PATENT DOCUMENTS

FR          1233947      10/1960

* cited by examiner

SYSTEM AND METHOD FOR IRRADIATING A TARGET WITH ELECTROMAGNETIC RADIATION TO PRODUCE A HEATED REGION

CROSS-REFERENCE TO RELATED APPLICATIONS AND CLAIM OF PRIORITY

This is a continuation-in-part of U.S. patent application Ser. No. 11/286,104 filed on Nov. 22, 2005, now U.S. Pat. No. 7,565,207, which is herein incorporated by reference.

BACKGROUND OF THE INVENTION

1. Field

The present invention relates generally to systems and apparatus for irradiating targets with electromagnetic radiation, and more specifically to systems having annular-type or various sectored applicators and associated control systems for controlling application of radiation to targets through phased array power steering, wherein the phased array system is integratable with a magnetic resonance imaging system.

2. State of the Art

Current systems for applying electromagnetic radiation (EMR) to targets, such as living bodies and biological tissue, and controlling the position of a region of heating within the target through phased array power steering are provided with a plurality of electromagnetic applicators powered by multi-channel EMR systems where different applicators are each provided with electronically controlled power of electronically controlled phase by different power channels of the EMR system. This creates a desired phased array heat pattern steering capability. Such an approach results in high system complexity and cost in order to provide such phased array heat pattern steering. The phased array devices have been integrated with magnetic resonance (MR) imaging systems and operated simultaneous and independent of the MR imaging system.

Several types of therapeutic treatments for cancer in humans are in current, common use. These treatments include surgery, X-rays, radiation from radioactive sources, and chemotherapy. These treatments are often combined in various ways to enhance treatment effectiveness.

Although such conventional treatment techniques have been successful in treating cancer in many patients and in prolonging the lives of many other patients, they are frequently ineffective against many types of cancer and often have severe adverse side effects at the necessary treatment levels. Protracted treatment of cancer patients by X-rays or chemotherapy, as an illustration, tends to eventually destroy or inhibit the patients' natural immunological systems to an extent that many patients eventually succumb to common infectious diseases, such as influenza or pneumonia, which otherwise probably would not be fatal. Also, many patients having advanced stages of cancer or complications may become too weak to withstand the trauma of surgical or other cancer treatments; hence, the treatments cannot be undertaken or must be discontinued.

Due both to the prevalence and the typically severe consequences of human cancer, as well as frequent ineffectiveness of current treatments such as those mentioned above, medical researchers are continually experimenting in an attempt to discover and develop improved or alternative cancer treatment methods with their associated treatment apparatus.

Hyperthermia, the generation of artificially elevated body temperatures, has recently been given serious scientific consideration as an alternative cancer treatment. Much research has been conducted into the effectiveness of hyperthermia alone or in combination with other treatment methods. This research is important in that hyperthermia techniques appear to have the potential for being extremely effective in the treatment of many or most types of human cancers, without the often severely adverse side effects associated with current cancer treatments. Hyperthermia is sometimes called thermal therapy indicating the raising of the temperature of a region of the body.

Researchers into hyperthermia treatment of cancer have commonly reported that many types of malignant growths in humans can be thermally destroyed, usually with no serious adverse side effects, by heating the malignancies to temperatures slightly below that injurious to most normal, healthy cells. Furthermore, many types of malignant cell masses have reportedly been found to have substantially lower heat transfer to lessen the ability to dissipate heat, presumably due to poorer vascularity and reduced blood flow characteristics. Consequently, these types of growths appear capable of preferential hyperthermia treatment. Poorly vascular malignant growths can reportedly be heated to temperatures several degrees higher than the temperature reached by the immediately surrounding healthy tissue. This promises to enable hyperthermic treatment of those types of malignant growths which are no more thermally sensitive than normal tissue without destruction of normal cells, and additionally to enable higher temperature, shorter hyperthermia treatment times of more thermally sensitive types of malignancies which exhibit poor vascularity, usually an advantage for important medical reasons.

In this regard, researchers have commonly reported that as a consequence of these thermal characteristics of most malignant growths and the thermal sensitivity of normal body cells, hyperthermia temperatures for treatment of human cancer should be carefully limited within a relatively narrow effective and safe temperature range. Hyperthermia is generally provided by temperatures over 40 degrees C. (140 degrees F.). Hyperthermia has historically included temperatures well above 60 degrees C., but in recent years has generally been considered to include temperatures as high as 45 degrees C. (113 degrees F.). However, there may be portions of a cancerous tumor that will exceed this level, the intent is to attempt to get as much of the tumor region above the 40 degree C. region as possible.

At treatment temperatures above the approximate 45 degrees C. (113 degrees F.), thermal damage to most types of normal cells is routinely observed if the time duration exceeds 30 to 60 minutes; thus, great care must be taken not to exceed these temperatures in healthy tissue for a prolonged period of time. Exposure duration at any elevated temperature is, of course, an important factor in establishing the extent of thermal damage to healthy tissue. However, if large or critical regions of the human body are heated into, or above, the 45 degree C. range for even relatively short times, normal tissue injury may be expected to result.

Historically, late in the last century alternating electric currents at frequencies above about 10 KHz were found to penetrate and cause heating in biological tissue. As a result, high frequency electric currents, usually in the megahertz frequency range, have since been widely used for therapeutic treatment of such common bodily disorders as infected tissue and muscle injuries. Early in this century, the name "diathermy" was given to this EMR tissue heating technique, and several discrete EMR frequencies in the megahertz range have subsequently been allocated specifically for diathermy use in this country by the Federal Communications Commission (FCC).

Extensive articles and reports have been written on the use of the phased array principle to provide hyperthermia heat pattern steering, and several patents have been issued covering use of phased arrays. All have relied upon the use of electronic phase and power steering to provide heat pattern steering control. This results in relatively complicated equipment configurations with multiple channel controls of power and phase. Such configurations can be difficult for routine clinical professionals to learn and utilize in the clinic. The simpler the clinical controls are in such a treatment system, the easier the operation of the system and potentially the greater the reliability. Simplicity of such designs may further lead to fewer system failures due to component failures. The utilization of standardized heating regions provided by standard energy steering configurations is expected to provide improved adaptation for clinical use.

The BSD-2000 system produced by BSD Medical Corporation, Salt Lake City, Utah, utilizes multi-channel phased array systems that control frequency, radiated power, and relative phase. Each channel has electronic controls of power and phase and is connected to different antennas. This allows electronic steering of the heating pattern, but at high cost and complexity. Such high cost can be cost prohibitive for routine clinical use. The ability to do heat pattern steering permits energy to be focused and directed more selectively to the target tumor region. In order to provide sufficient heat energy penetration, a lower frequency must be selected. This is because the penetration attenuation of human tissue increases at higher frequencies. As frequency is lowered however, the heating focus diameter increases. Thus, the proper frequency is needed to provide the optimum depth within acceptable heating pattern size limits. In general, hyperthermia is best applied when tumor target tissues around the diseased area is also heated. This provides preheating of inflowing blood and reduces thermal conduction from the perimeter of the tumor to draw heat out of the tumor perimeter. The BSD-2000 system has been investigated since 1988. The novel use of such phased arrays systems has proven to be useful and beneficial in treating patients with various forms of cancers, even in Phase III clinical trials. However, the use of complex and expensive multi-channel amplifier systems to provide multiple EMR synchronous phase energy channels that have phase control to steer the heating region in the body has excessive complexity for routine clinical use in some treatment centers. The BSD-2000-3D/MR system is the integration of the BSD-2000-3D hyperthermia system with a magnetic resonance imaging system. In such a configuration the hyperthermia system has been operated independent of the MR imaging system, where the MR imaging system has been used as an independent monitor primarily of temperature. This has been done using the proton resonance shift from the image stored prior to body heating and digitally subtracting the phase image of the initial pattern from the complex phase image patterns obtained during heating. This provides generally a dominant indication of the temperature change in tissues of the body. This temperature change image produced by the MR imaging system can include error effects that are produced by tissue perfusion changes during heating treatments. The perfusion changes can also be determined by the MR imaging system.

There is a need for EMR applicator apparatus, and corresponding methods for EMR irradiation, which provide simplified heat pattern steering of EMR heating in a target, such as a target of biological tissue in a living body or tissue simulating matter.

SUMMARY OF THE INVENTION

It has been observed that the typical operating frequency of a phased array device located in a magnetic resonance imaging system can range between 60 to 200 MHz. The typical magnetic imaging system operated with a magnetic field strength of approximately 1.5 Tesla typically uses radio frequency (RF) power transmitters at a frequency of 63.5 MHz. For a field magnetic strength of approximately 3 Tesla, the transmitter frequency is typically set to 127 MHz. The high power RF transmitter frequency of the MR system is in the same range as that used for the phased array hyperthermia device. To simplify such an integrated system of the phased array hyperthermia with the MR imaging system, it is proposed to provide a novel method to utilize the MR RF power output to also provide the needed power to heat the target using the phased array hyperthermia device that is inserted into the MR aperture.

According to the present invention, a simplified hyperthermia system utilizing an array of electromagnetic radiation applicators utilizes variable reflective termination devices coupled to the applicators to control the phase of the EMR power applied to the individual applicators to steer and control the position of the system heating region in the target. The EMR power can be supplied to the applicators by a single EMR power source and the phase of the EMR radiation directed toward the target by each of the individual applicators is controlled by the variable reflective termination devices. The state of a variable reflective termination device, e.g., whether the termination presents an open circuit or a short circuit, can be easily varied by a user of the system to control the phase of reflected EMR power at the connection to the applicator, which controls the phase of the radiation from the particular applicator. By controlling the phase of the radiation from each applicator in this manner, the position of the heated region in the target can be steered and controlled without the need for a separate power channel in the EMR power source for each applicator. A single EMR energy source with a passive power splitter can be used to supply EMR energy of approximately equal power and phase to all applicators through the power splitter and the phase of energy radiated by each individual applicator is easily controlled by the variable reflective termination device.

In one embodiment of the present invention, a simplified hyperthermia system integrated with a magnetic imaging system having an array of electromagnetic radiation applicators utilizes variable reflective termination devices coupled to the applicators to control the phase of the EMR power applied to the individual applicators to steer and control the position of the system heating region in the target and being energized by the RF power output of the MR imaging system. The EMR power can be supplied to the applicators by a single EMR power coupling device or by an array of coupling sources that can be inserted into the aperture of the MR imaging system. The phase of the EMR radiation directed toward the target by each of the individual applicators can be controlled by the variable reflective termination devices.

The state of a variable reflective termination device, e.g., whether the termination presents an open circuit or a short circuit, can be varied by a user of the system to control the phase of reflected EMR power at the connection to the applicator, which controls the phase of the radiation from the particular applicator. By controlling the phase of the radiation from each applicator in this manner, the position of the heated region in the target can be steered and controlled without the need for a separate power channel in the EMR power source for each applicator. A single EMR energy coupling device with a passive power splitter can be used to supply EMR energy of approximately equal power and phase to all applicators through the power splitter. The phase of energy radiated by each individual applicator can be controlled by the variable reflective termination device. Multiple coupling devices can also be used to provide the EMR power to individual or groups of radiating EMR applicators.

In one embodiment, the EMR power source can be coupled to all applicators in the array. Alternatively, some of the applicators in the array can be parasitic applicators, i.e., not directly coupled to the EMR power source. These non-active, parasitic applicators can re-radiate EMR energy with the phase of the re-radiated energy dependent upon the termination of the applicator. The termination can be made adjustable by connection of a variable reflective termination device coupled to the parasitic applicator. This phase control can also be provided by a number of means, such as path length variation, and the use of using a number of PIN diodes that can be turned on to provide a short between two transmission line conductors used for tuning or phase shifting.

In one embodiment, the variable reflective termination devices can be coupled to each applicator in the array. However, depending upon the adjustability of the heating region positioning required or desired, it is not necessary to connect a variable reflective termination device to each applicator. As a minimum, it is only necessary that one applicator be coupled to the EMR power source and that only one applicator be connected to a variable reflective termination device. If only one applicator is coupled directly to the power source, the variable reflective termination device will need to be coupled to a different applicator to provide the system with some steering capability. The coupling of the applicator(s) to the power source can include use of the EMR power source of a magnetic resonance imaging system by either direct coaxial cable coupling means such as coaxial switches or PIN diode switches or by other coupling means from the transmitting body coil.

The applicator array of the invention will usually be formed of a plurality of individual applicators for directing EMR energy toward the target. The EMR power source is coupled to supply EMR energy to one or more of the individual applicators, which are the primary radiators. The power source can be controlled to control the amplitude and phase of energy supplied by the power source to the primary radiators. The power source can be a high output power, single channel power source that uses a passive power splitter to activate the primary radiators with EMR power of approximately equal power and phase. In one embodiment, all applicators can be primary radiators coupled to the power source through the power splitter. Alternatively, some of the applicators can be parasitic non-active, passive radiators that re-radiate EMR energy. The power and phase of this re-radiated energy is determined by the terminations of the parasitic applicators. Variable reflective termination devices preferably provide the termination of the passive applicators and the state of the variable reflective termination devices determine the phase of the re-radiated energy and the resulting heating pattern of the applicator array.

In one embodiment, four primary radiators are positioned around a target to be radiated. All radiators are primary radiators coupled to a single channel, high power EMR power source through a passive power splitter that splits the EMR power from the source into four separate channels of approximately equal power and phase. The applicators each include at least one antenna and each have a central energy supply connection point. Each applicator is coupled to the power splitter by a cable of predetermined length extending from the power splitter to the applicator central energy supply connection point. Each applicator central energy supply connection point is thus provided with a signal having approximately equal power and equal phase through the power splitter from the EMR power source. The length of the cable between the central energy supply connection point and the variable reflective termination device and the state of the variable reflective termination device determine the apparent state of the central energy supply connection point to incoming EMR power and determines the phase of the EMR energy radiated from the antennas of the applicator. This arrangement provides offset heat pattern steering toward the surface of the body while preserving significant deep heating energy penetration. It provides control to direct the region of heating away from a centered region in the target. For example, in one embodiment, an array of antennas can be used to provide eight offset positions rotated forty-five degrees around the target from one another. The target will usually be a human patient or tissue sample to be heated which is positioned in a housing. The applicators can be arranged around the housing to encircle the target placed in the housing. A dielectric fluid having an impedance approximately equivalent to an applicator impedance at the predetermined frequency of the EMR radiation being used in the system can be used to substantially fill a predetermined length of the housing around the target. The housing will generally include a bolus inside the housing around the target to contain the fluid.

In another embodiment that would include a magnetic resonant imaging system, four or more primary radiators are positioned around a target to be radiated. All radiators are primary radiators coupled to a single EMR coupler. The EMR coupler is coupled to the magnetic imaging Body Coil providing the high power EMR through a passive power splitter that splits the EMR power from the MR coupling source into four separate channels of approximately equal power and phase. The applicators each include at least one antenna and each have a central energy supply connection point. Each applicator is coupled to the power splitter by a cable of predetermined length extending from the power splitter to the applicator central energy supply connection point. Each applicator central energy supply connection point is thus provided with a radio frequency signal having approximately equal power of equal phase through the power splitter from the EMR power source.

Each applicator can be connected to a variable reflective termination device through a cable of predetermined length that is also connected to the central energy supply connection point or to a variable electrical length device such as a variable phase delay transmission device typically called a passive phase shifter. The length of the cable between the central energy supply connection point and the variable reflective termination device and the state of the variable reflective termination device determine the apparent state of the central energy supply connection point to incoming EMR power and determines the phase of the EMR energy radiated from the antennas of the applicator. This arrangement can provide offset heat pattern steering toward the surface of the body while preserving significant deep heating energy penetration. It provides control to direct the region of heating away from a centered region in the target. For example, in one embodiment the arrangement can be used to target eight offset positions rotated approximately forty-five degrees around the target from one another. The target will usually be a human patient or tissue sample to be heated which is positioned in a housing.

The applicators can be arranged around the housing to encircle the target placed in the housing. The EMR coupling device from the magnetic resonance imaging system high power EMR amplifier can be either directly connected to the applicator array or coupling can be achieved by a coupling device to the body coil in the MR imaging device. The EMR coupling device can be placed in close proximity to the body coil to provide for efficient coupling of the EMR power from the body coil. The coupling device can utilize the standard activation mode of the body coil to pass energy into the coupling device that is directed to the radiating applicator. The connections between the EMR coupler and the feed points of the applicator phased array can be arranged in such a way that when the MR transmitting mode is active for image acquisition, the connections to the applicators are opened so that the applicators do not load the EMR power of the body coil during that time period. Such opening can be obtained by using PIN diodes to provide an open and closed circuit path. A dielectric fluid having an impedance approximately equivalent to the impedance of the body allows an applicator impedance to be matched to the body at the predetermined frequency of the EMR radiation being used in the system. The bolus can be used to substantially fill a predetermined length of the housing around the target. The housing will generally include a bolus inside the housing around the target to contain the fluid. In one embodiment, the fluid can be deionized water.

Rather than four separate applicators in the system described, a single applicator formed by two concentric metallic cylinders surrounding the target can be used and can be configured to have the same EMR energy steering as described above. The steering is provided by placing variable reflective termination devices between the two concentric rings at spaced intervals around the rings so that the devices can provide an equivalent short circuit termination between the two metal rings to steer the energy away from the short. This short circuit configuration can be achieved by joining common ends of the dipoles or filling the spaces partially or totally between the adjacent dipole ends.

The system can utilize different types of EMR applicators to heat the target. The individual applicators may be, for example, horn type radiators, patch radiators, dipole antennae, folded dipoles, monopoles, waveguides, two concentric metal cylinders that surround the target to form a single dipole, etc. These antenna sources can be linearly polarized for the greatest enhancement of the heating in the overlapping wave targeted region. In another embodiment, circularly or elliptically polarized spirals can also be used for the EMR radiating sources.

The system of the present invention can be used to provide lower cost and complexity for phased array control of heating patterns in predictable steering positions in a target through the use of variable reflective termination devices to select and control the reflective terminations of at least one of the applicators in an array. In another embodiment, the present invention can be included with a magnetic resonance imaging system that can provide lower cost and complexity for phased array control of heating patterns in predictable steering positions in a target through the use of variable reflective termination devices to select and control the reflective terminations of at least one of the applicators in an array when combined with an magnetic resonance imaging system since the expensive high power EMR amplifiers used for the Body Coil can be used for both the imaging and the tissue heating. The variable reflective termination devices can include open circuit and short circuit terminations, variable cable lengths, or similar devices. These devices can also be used to create the same effects with parasitic antennas or combinations of primary and parasitic antennas for phase steering of a phased array of antennas. The present invention can provide a simplified annular applicator apparatus for EMR heating for any required purpose, such as medical hyperthermic treatment of cancer or of other medical uses or research.

THE DRAWINGS

Additional features and advantages of the invention will be apparent from the detailed description which follows, taken in conjunction with the accompanying drawings, which together illustrate, by way of example, features of the invention; and, wherein.

Figure 1:
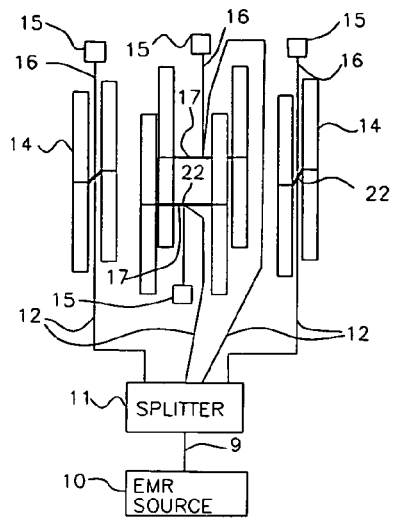
FIG. 1 is a schematic diagram of a system of the invention for creating hyperthermia in a target using active energy at feed points of an antenna applicator array with variable phase terminations used to alter the resultant phase radiated from each antenna group.
Figure 5:
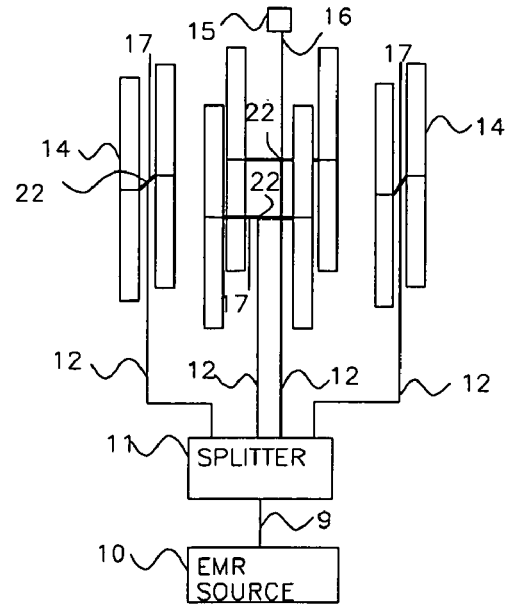
Figure 6:
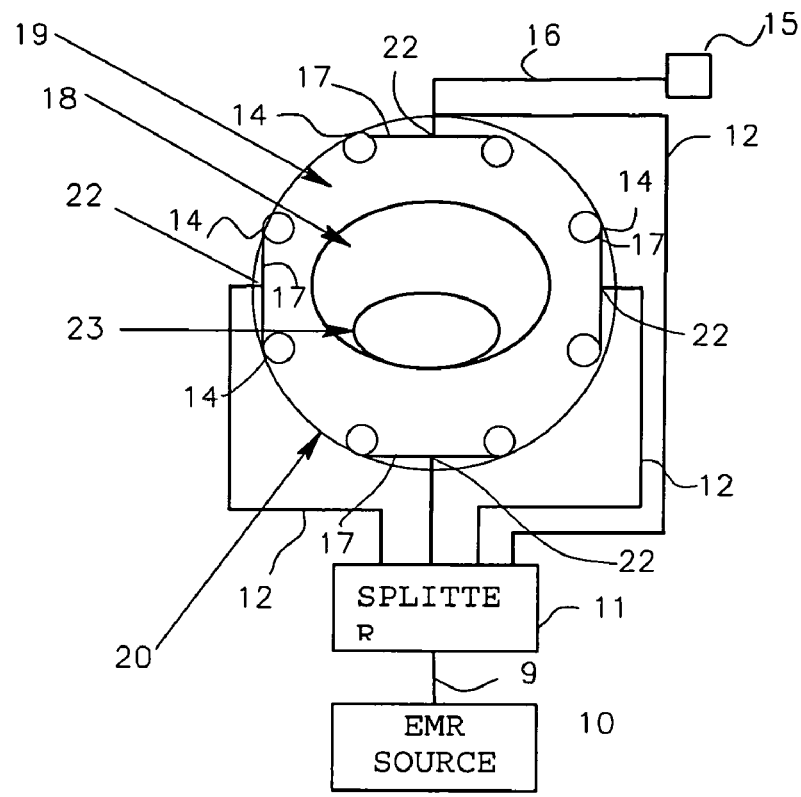
Figure 7:
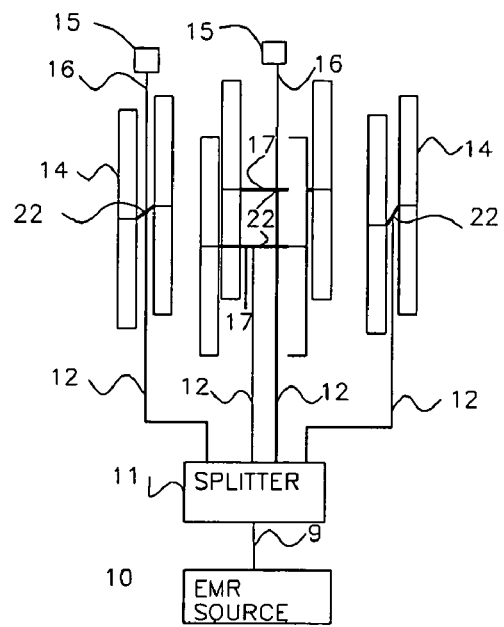
Figure 8:
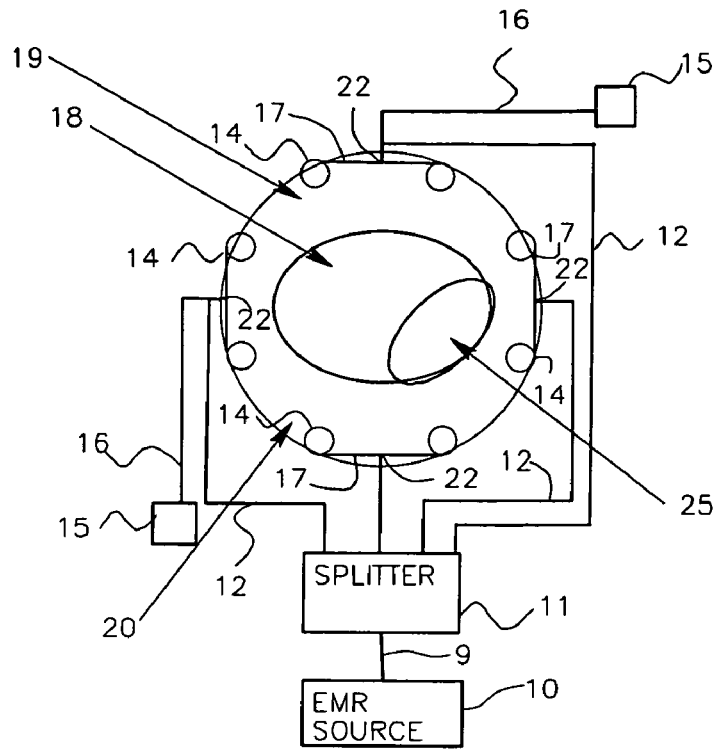

FIG. 5 is a diagram similar to that of FIG. 1, but showing a phased array system with limited phase steering capability with a variable reflective termination device coupled to one of the applicators at its feed point so the phase of the termination can be altered to steer the resulting heating pattern created by the system in a body either toward or away from the applicator with the termination device;

FIG. 6 is a schematic top view of the system of FIG. 5 showing an elliptical target body centrally located inside a cylindrical housing and antenna array and showing the steered heated area displaced in the body away from the applicator with the termination device;

FIG. 7 is a diagram similar to that of FIG. 1, but showing a phased array system with limited phase steering capability with a variable reflective termination device coupled to two adjacent applicators at their feed points so the phase of the termination can be altered to steer the resulting heating pattern created by the system in a body either toward or away from the applicators with the termination devices;

FIG. 8 is a schematic top view of the system of FIG. 7 showing an elliptical target body centrally located inside a cylindrical housing and antenna array and showing the steered heated area displaced in the body away from the two adjacent applicators with the termination devices.

Figure 2:
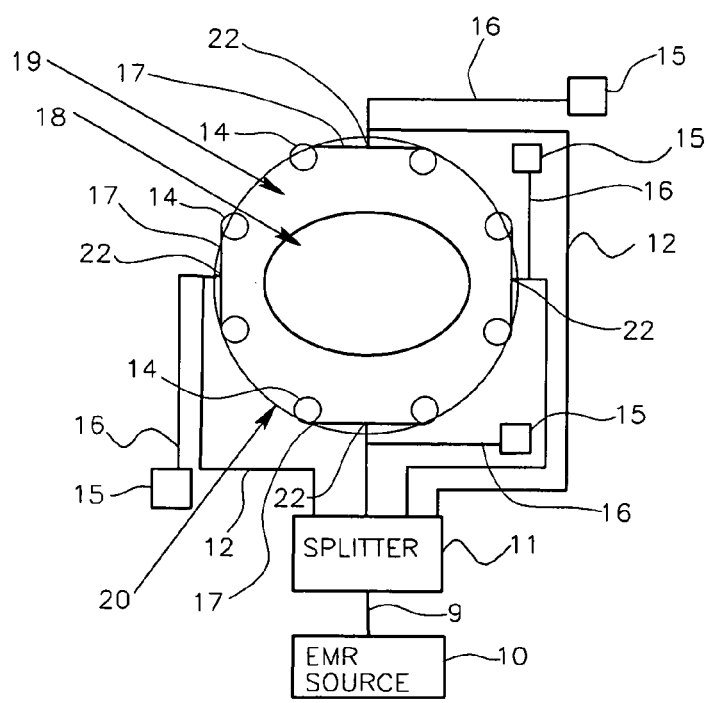
FIG. 2 is a schematic top view of the system of FIG. 1 showing an elliptical target body centrally located inside a cylindrical housing and antenna array.
Figure 9:
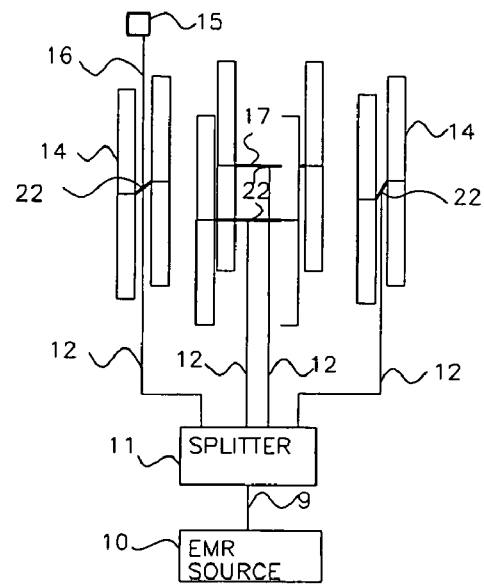
Figure 10:
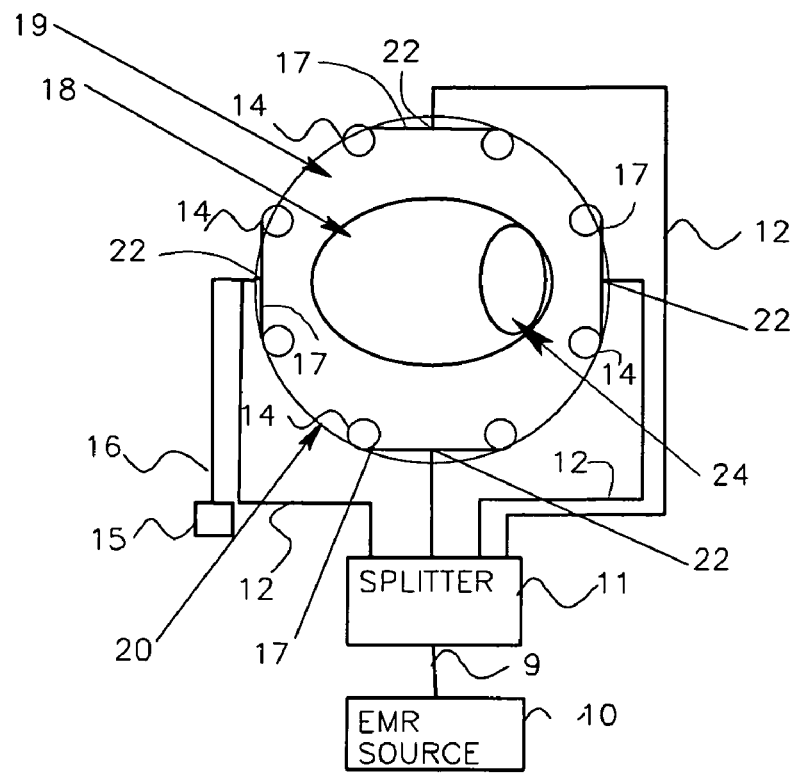
Figure 11:
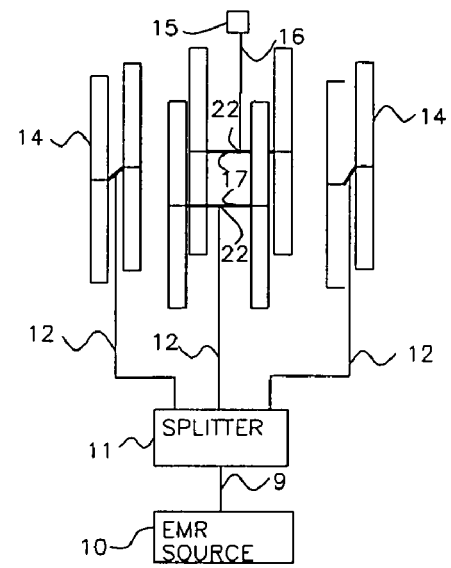
Figure 12:
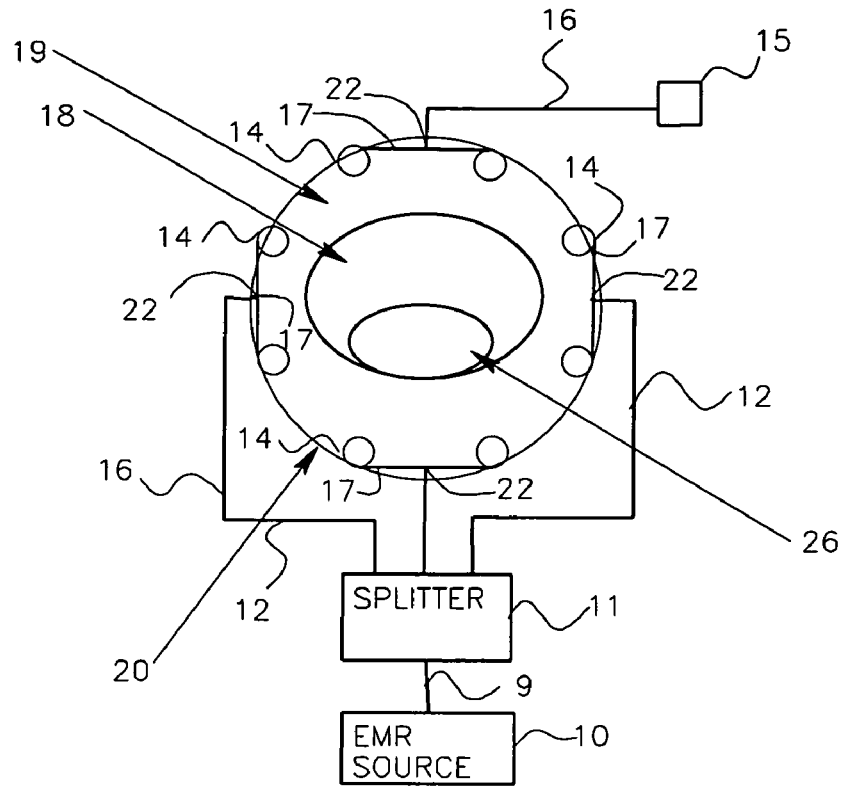
Figure 13:
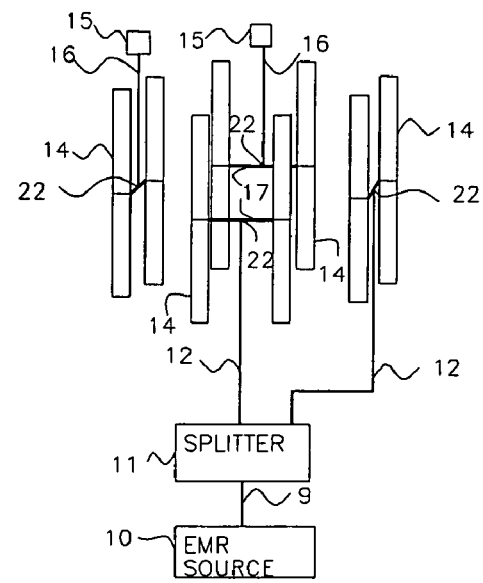
Figure 14:
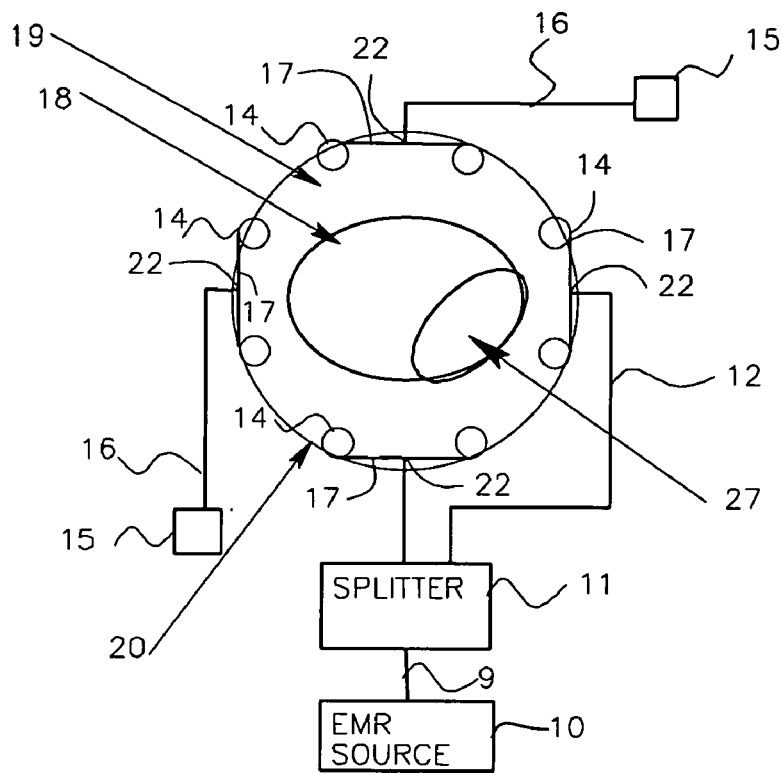
Figure 15:
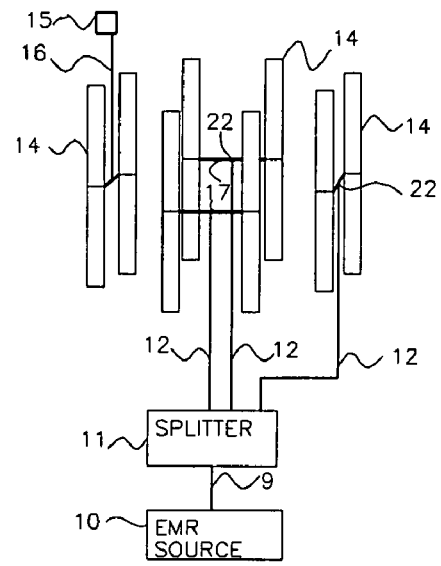
Figure 16:
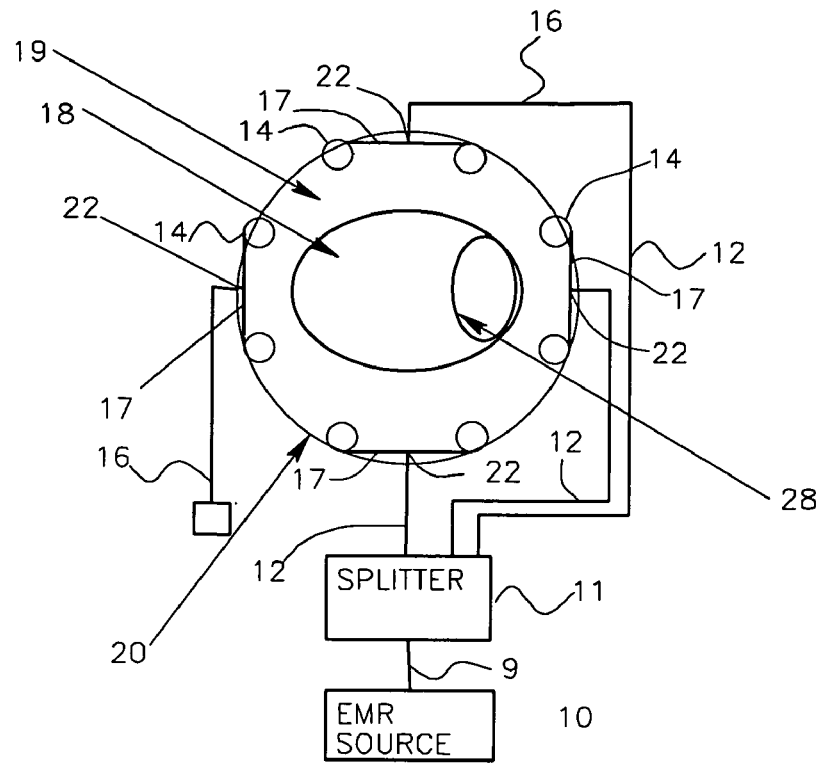
Figure 17:
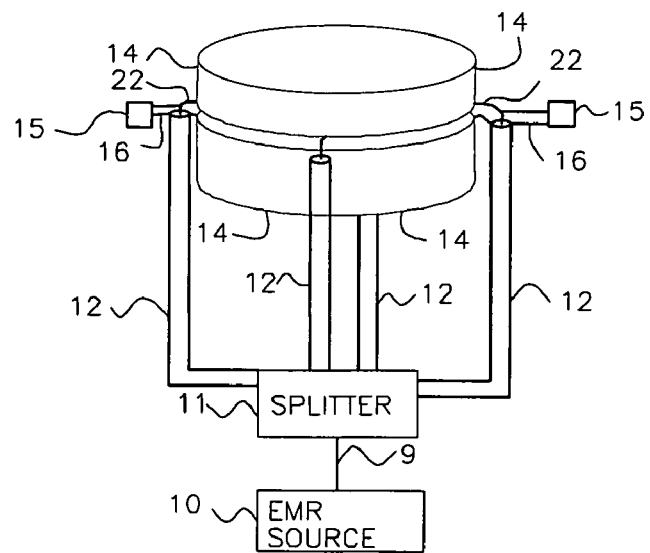
Figure 18:
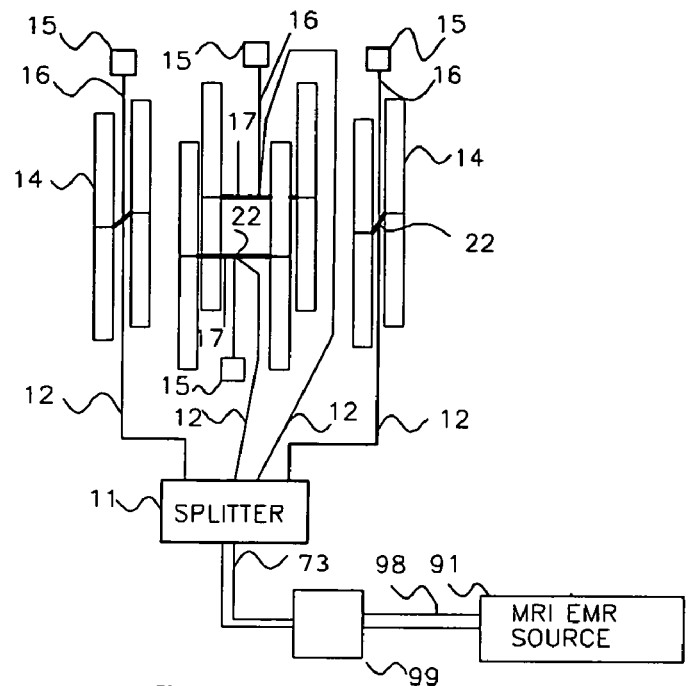
Figure 19:
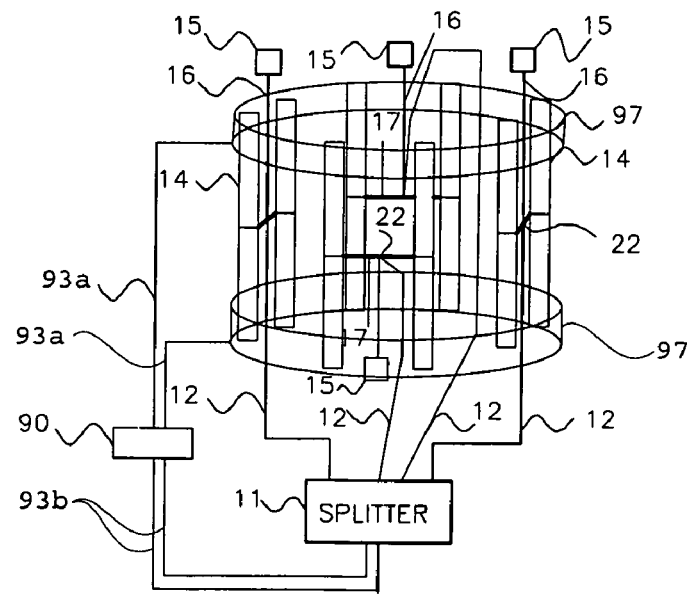
Figure 20:
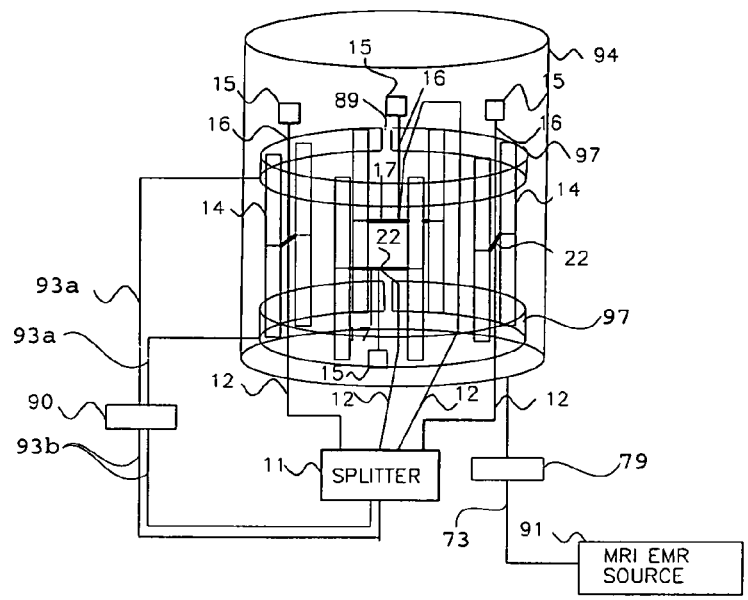
Figure 21:
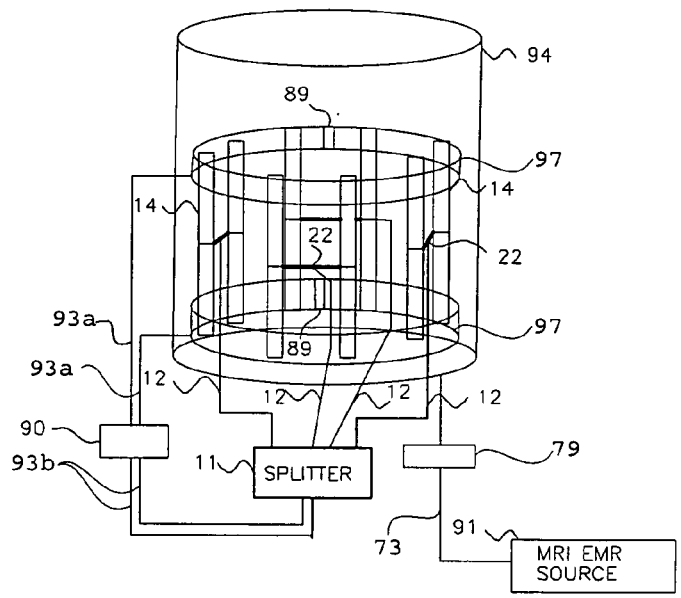
Figure 22:
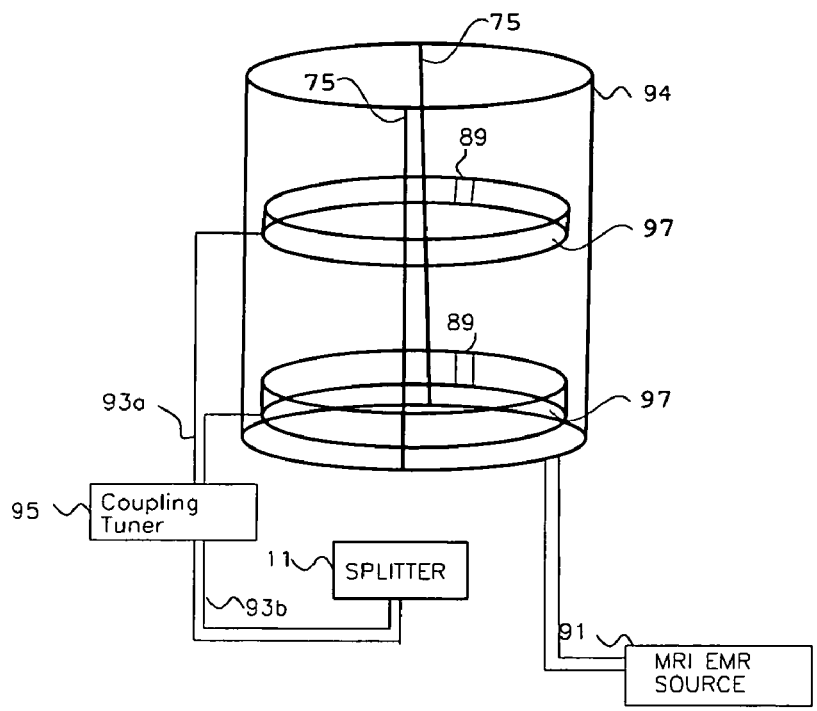
Figure 23:
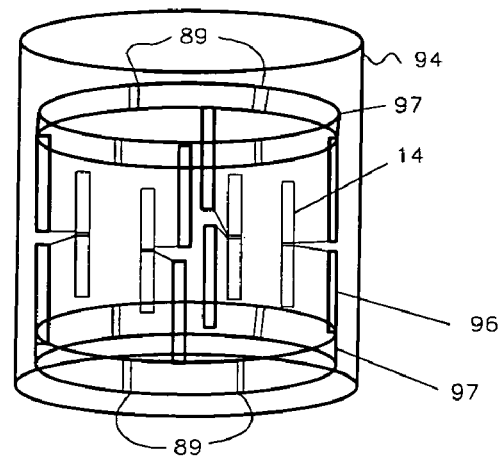
Figure 24:
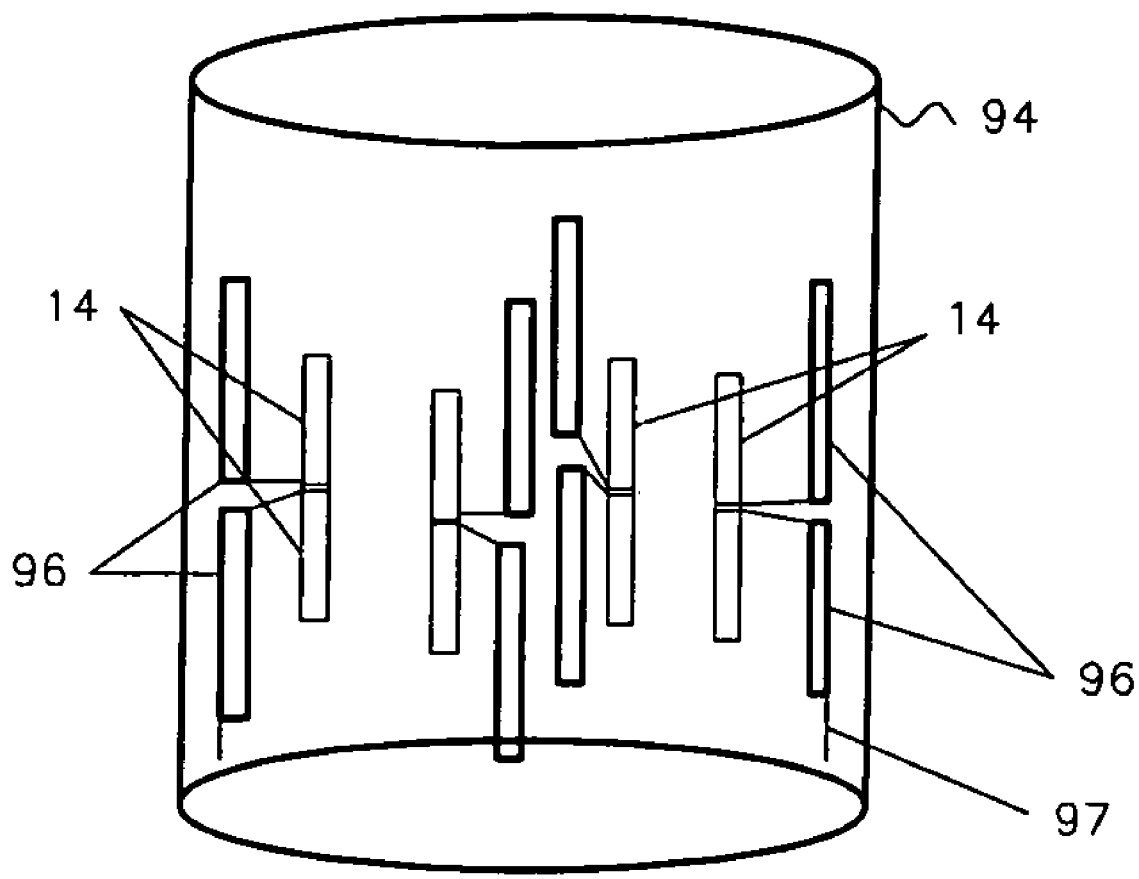
Figure 25:
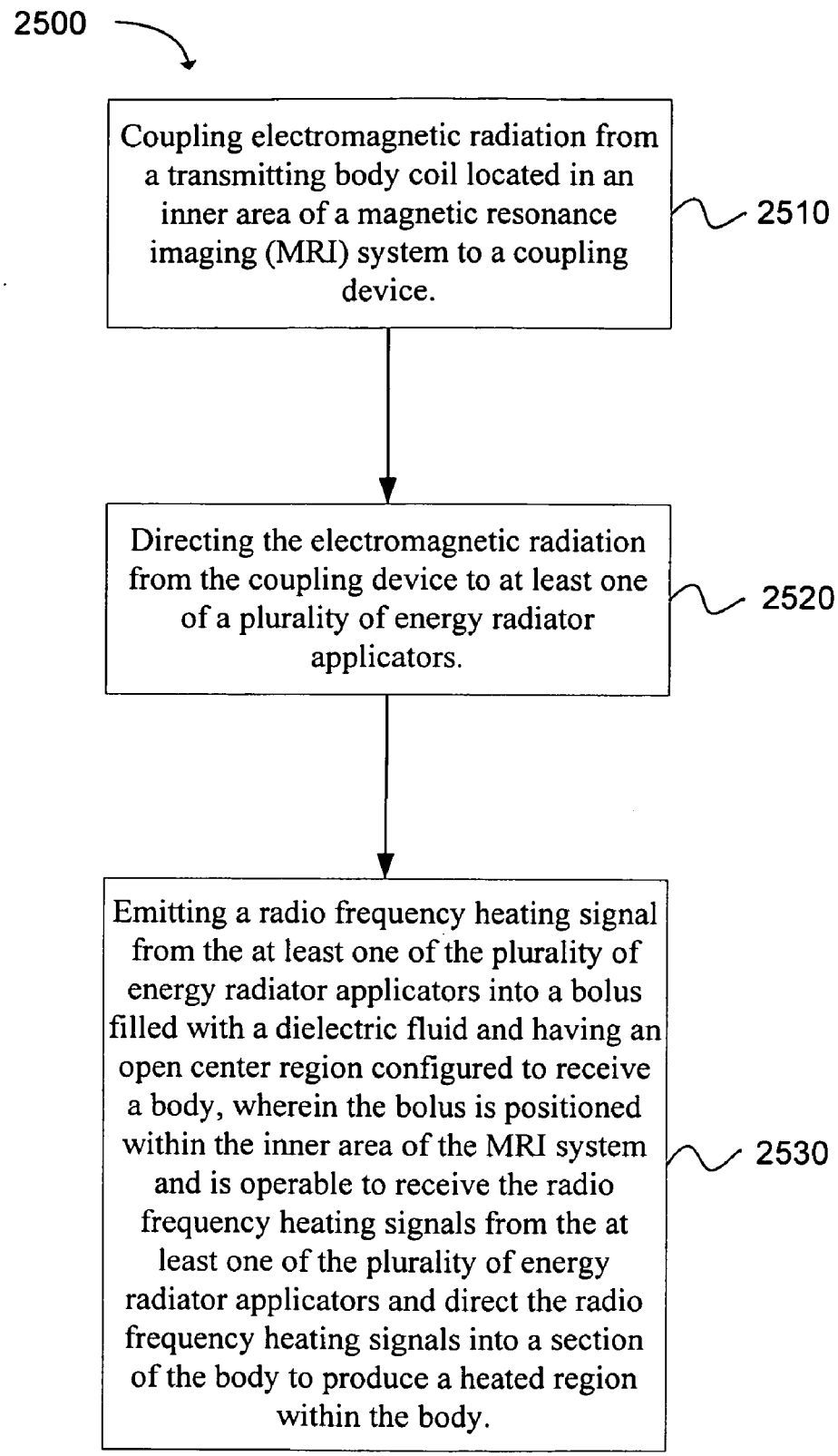

FIG. 9 is a diagram similar to that of FIG. 5, showing a similar phased array system with limited phase steering capability with a variable reflective termination device coupled to a different one of the applicators at its feed point so the phase of the termination can be altered to steer the resulting heating pattern created by the system in a body either toward or away from the applicator with the termination device;

FIG. 10 is a schematic top view of the system of FIG. 9 showing an elliptical target body centrally located inside a cylindrical housing and antenna array and showing the steered heated area displaced in the body away from the applicator with the termination device;

FIG. 11 is a diagram similar to that of FIG. 5, showing a similar phased array system with limited phase steering capability with one applicator having only a variable reflective termination device connected at its feed point with no connection to the EMR energy source at its feed point so the phase of the termination can be altered to steer the resulting heating pattern created by the system in a body either toward or away from the applicator with the termination device;

FIG. 12 is a schematic top view of the system of FIG. 11 showing an elliptical target body centrally located inside a cylindrical housing and antenna array and showing the steered heated area displaced in the body away from the applicator with the termination device;

FIG. 13 is a diagram similar to that of FIG. 7, but showing a phased array system with limited phase steering capability with two adjacent applicators having only a variable reflective termination device connected at their feed points with no connection to the EMR energy source at their feed points so the phase of the terminations can be altered to steer the resulting heating pattern created by the system in a body either toward or away from the applicators with the termination devices;

FIG. 14 is a schematic top view of the system of FIG. 13 showing an elliptical target body centrally located inside a cylindrical housing and antenna array and showing the steered heated area displaced in the body away from the two adjacent applicators with the termination devices;

FIG. 15 is a diagram similar to that of FIG. 11, showing a similar phased array system with limited phase steering capability with a different one of the applicators having only a variable reflective termination device connected at its feed point with no connection to the EMR energy source at its feed point so the phase of the termination can be altered to steer the resulting heating pattern created by the system in a body either toward or away from the applicator with the termination device;

FIG. 16 is a schematic top view of the system of FIG. 15 showing an elliptical target body centrally located inside a cylindrical housing and antenna array and showing the steered heated area displaced in the body away from the applicator with the termination device;

FIG. 17 is a schematic diagram of a system of the invention with full steering capability similar to the system shown in FIG. 1 but showing an applicator formed of two concentric metal cylinders that surround the target forming a single dipole with localized EMR signal feed connections between the cylinders at four points spaced at ninety degree intervals around the cylinders and with variable reflective termination devices coupled to each feed point between the two cylinders to provide steering similar to that provided by the system of FIGS. 1 and 2;

FIG. 18 is a schematic diagram of a system having a plurality of electromagnetic radiation applicators powered by an MRI EMR source through a switch in accordance with an embodiment of the present invention;

FIG. 19 is a schematic diagram of a system having a coupling device operable to couple EMR from a transmitting body coil in an MRI and direct the EMR to a plurality of electromagnetic radiation applicators in accordance with an embodiment of the present invention;

FIG. 20 is a schematic diagram of the system of FIG. 19 showing the transmitting body coil in relation to the coupling device and the plurality of electromagnetic radiation applicators and a switch used to open and close the circuit path between the body coil and the coupling device;

FIG. 21 is a schematic diagram of the system of FIG. 20 without the variable reflective termination devices;

FIG. 22 is a schematic diagram of a system having a coupling device that includes coupling rings with breaks to couple the EMR from the body coil of the MRI in accordance with an embodiment of the present invention;

FIG. 23 is a schematic diagram of a system having a coupling device that includes coupling rings with breaks and resonant coupling dipoles to couple the EMR from the body coil of the MRI in accordance with an embodiment of the present invention;

FIG. 24 is a schematic diagram of resonant dipole couplers used to couple the EMR from the body coil of the MRI in accordance with an embodiment of the present invention; and FIG. 25 is a flow chart depicting a method for irradiating a target with electromagnetic radiation to produce a heated region in accordance with an embodiment of the present invention.

DETAILED DESCRIPTION OF THE ILLUSTRATED EMBODIMENTS

The apparatus of the invention, as shown in FIG. 1, includes an electromagnetic radiation (EMR) energy source 10 connected to a power splitter 11 that splits the EMR energy from source 10 into a plurality of outputs each connected to one of a plurality of applicators each including one or more antennas 14 connected by cables 17 and having central energy supply connection points 22. The antennas 14 radiate the EMR energy into a body 19, FIG. 2, positioned inside a dielectric shell or housing 20 for heating a target area in the body 19. The radiated energy from the antennas is referred to as a radio frequency heating signal.

The EMR energy source 10 generally provides EMR energy in a frequency from 40 to 1000 MHz. For heating in human adult torso regions, the preferred frequencies are from 40 to 200 MHz. This is because the penetration losses and the localized heating capability at these frequencies provide for selective targeting and steering in useful regions with adequate penetration to heat deeply. The power splitter 11 is a passive power splitter configured without internal loss generally for more efficient operation. This then provides energy that is directed to an antenna group to be partially or totally reflected with various phases to alter the location of the phase focusing in the body. The EMR source 10 is connected to the power splitter 11 using a coaxial transmission line 9. The power received by splitter 11 is divided between the output coaxial ports, here shown as four coaxial output ports, based upon the impedance presented to the passive power splitter by each of the output coaxial cables 12. The cables 12 are used to connect the power from the power splitter 11 to the central energy supply connection points or feed points 22 of each applicator, here shown as four applicators, that are each comprised of single or multiple antennas 14 connected by cables 17. At these feed points 22, there are additional coaxial cables 16 that are used to attach to variable reflective termination devices 15. These variable reflective termination devices control the effective termination seen at the central energy supply connection points 22.

The variable reflective termination devices 15 can be, for example, coaxial shorts or coaxial opens where changing a termination from an electrical short circuit to an electrical open circuit will alter the reflected phase by one hundred eighty degrees to provide differing phase steering effects. If the effective termination 15 for example is a short circuit and is connected by a cable 16 that is one quarter wave length long, the effect of that short circuit appears as an open circuit at the feed point 22 and provides for a central focal region of the heating pattern. This same result will occur if cable 16 is one quarter, three quarters, one and one quarter, one and three quarters, etc. in length. However, when this variable termination is changed to an open circuit at the end of the quarter wave length cable 16, the resulting heating pattern is steered away from that applicator or antenna region as the effective termination at the feed point is that of a short circuit. In this case, the energy provided to the feed point 22 from this effective short is reflected back through the coaxial cable 12 to the power splitter 11. When the reflective energy arrives at the power splitter 11, the cable length 12 should be chosen so that the reflected phase from the variable termination 22 approximately appears as an open circuit so that it does not alter the phase or the impedance matching of other splitter ports, but just reflects its power back to the splitter 11 to be redirected out of the other splitter ports. If this reflected phase from the feed point termination 15 that places a short at the feed point 22 would appear as a short circuit at the junction internal to the splitter 11, then the splitter 11 would reflect too much power back to the EMR source 10. Therefore, the length of the cables 12 should be a quarter wave length long or an odd multiplier of a quarter wave length (¼, ¾, ⁵⁄₄, ⁷⁄₄, ⁹⁄₄, etc.). This will assure that a short circuit at the feed point 22 will appear as an open circuit at the splitter 12. When the termination 15 in this example places the equivalent of an open circuit at the feed point 22, then the impedance from the antenna group associated with that channel will reflect a termination impedance of the radiating antennas (typically 50 ohms so the coaxial cable line is impedance is matched). This reflection that appears as an open circuit at 11 from an effective short termination at the feed point 22 will cause a partial mismatch of impedance in the splitter 11, but this will not significantly alter the impedance match provided to the EMR source 10 for a power splitter 11 having four or more output cables 12.

If the termination example is changed so that cables 16 are an integral number of half wavelengths, then the termination to provide an effective short at the feed point 22 would need to be a short circuit. This is because a short circuit appears as a short circuit impedance at a half wavelength from the short termination.

FIG. 2 is a top view of the arrangement of FIG. 1 that shows a diagrammatic cross-sectional view of the elliptical section 18 representing the human body as a target for radiation heating. The body 18 is surrounded by a housing or high dielectric shell 20 with the applicators spaced around the shell or housing 20 to surround the target body 18. The body 18 is typically surrounded by a high dielectric region fluid, such as water, filling the space 19 between the target body 18 and the dielectric shell 20. Dielectric shell or housing 20 is preferred to be a clear plastic tube. The plastic tube 20 can be cylindrical, elliptical, oval shaped, made by two circular arcs, or in a form of several flat sections such as an octagon or pentagon. Usually a bolus formed by a closed flexible plastic bladder, not shown, is positioned in the housing 20 around target body 18 to easily hold and contain the high dielectric fluid in the high dielectric region fluid area 19. FIG. 2 also shows the four variable reflective phase termination devices 15 as shown in FIG. 1.

Figure 3:
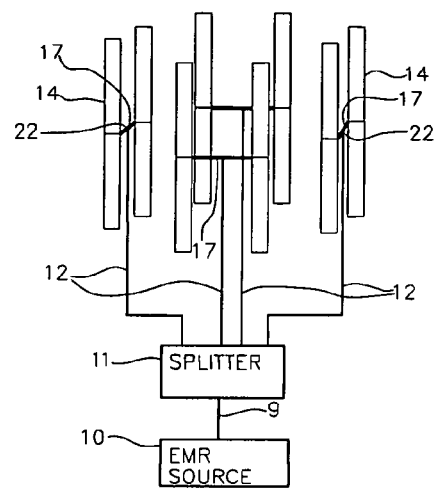
FIG. 3 is a diagram similar to that of FIG. 1, but showing a phased array system with no phase steering capability using a single electromagnetic energy source and power splitter that would provide only a central region of heating within the targeted tissue.
Figure 4:
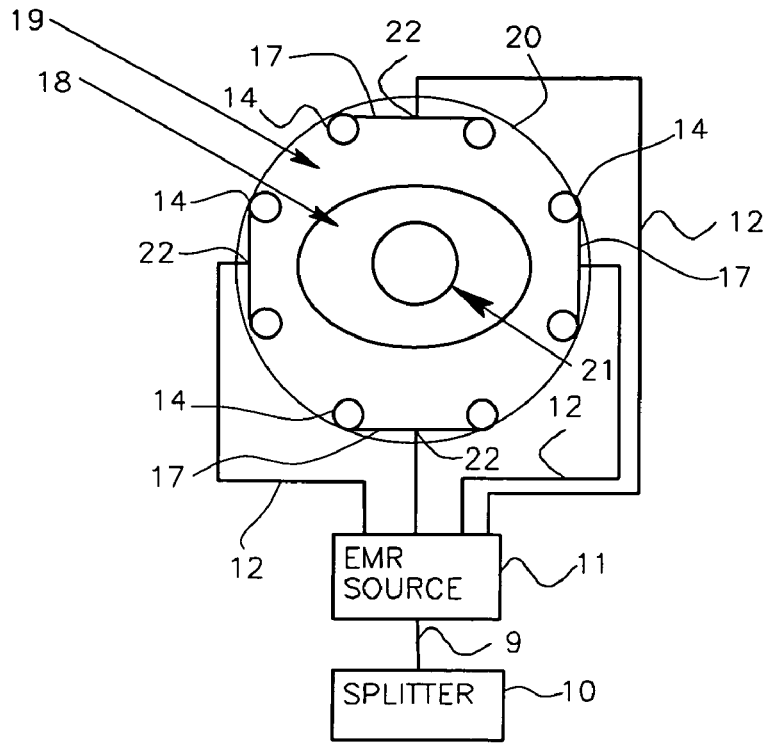
FIG. 4 is a schematic top view of the system of FIG. 3 showing an elliptical target body centrally located inside a cylindrical housing and antenna array and showing the centrally located heated area in the body.

FIGS. 3 and 4 are the same as described in the details of FIGS. 1 and 2, but with no variable reflective termination devices 15 of FIGS. 1 and 2. In this arrangement, equal phase is provided at all feed points 22. This arrangement without any variable reflective termination devices 15 has no heating region steering capability and provides only a central heating region for the apparatus as shown by central heating region 21 in body 18 in FIG. 4. This represents and is equivalent to setting all of the variable reflective phase termination devices 15 in FIGS. 1 and 2 to provide the same or equal phase at all feed points 22. Such would be the case, for example, if all four variable reflective termination devices 15 in FIGS. 1 and 2 are set to provide an equivalent open circuit at all feed points 22.

FIG. 4 is a top view of the arrangement of FIG. 3 that shows a diagrammatic cross-sectional view of the elliptical section 18 representing the human body. Again, the body is typically surrounded by a high dielectric region fluid, such as water, filling the space 19 between the body 18 and the dielectric shell 20, that is preferred to be a clear plastic tube. The plastic tube can be cylindrical, elliptical, oval shaped, made by two circular arcs, or in a form of several flat sections such as an octagon or pentagon. FIG. 4 shows the central heating region 21 in body 18 that is produced when equal phases are provided to all applicator feed points 22.

FIGS. 5 and 6 are the same as described in the details of FIGS. 1 and 2, but with only one of the variable reflective termination devices 15 of FIG. 1. In this arrangement, equal phase is provided at the three feed points 22 without the variable reflective termination devices. The phase at the feed point 22 having the variable reflective termination device connected thereto can be adjusted to provide a different phase from the phase at the other three feed points. This provides steering capability, and when the variable reflective termination device 15 is set to provide a different phase from the phase at the other three feed points, provides a displaced heating region 23, FIG. 6, for the apparatus. These FIGs. are equivalent to FIGS. 1 and 2 having three of the variable reflective termination devices 15 set to provide the same phase to three of the feed points 22 and one of the variable reflective termination devices 15 set differently to provide a different phase to the fourth feed point. For example, one of the termination devices in FIGS. 1 and 2 can be set to provide a short circuit at the connected feed point 22 and the remaining termination devices all set to provide an open circuit to the remaining feed points 22.

FIG. 6 is a top view similar to that of FIG. 4, but shows the arrangement of FIG. 5. The heating zone or region 23 represents the approximate heating zone that would result from the variable termination device 15 being adjusted to provide an equivalent short circuit at the attached feed point 22 while the remaining feed points 22 are all provided an equivalent open circuit.

FIGS. 9 and 10 are similar to FIGS. 5 and 6 showing only one of the variable reflective termination devices of FIG. 1, but showing the variable reflective termination device connected to a different feed point 22 than shown in FIGS. 5 and 6. In this arrangement, as in the arrangement of FIGS. 5 and 6, equal phase is provided at the three feed points 22 without the variable reflective termination devices. The phase at the feed point 22 having the variable reflective termination device connected thereto can be adjusted to provide a different phase from the other three feed points. This also provides a displaced heating region 24, FIG. 10, for the apparatus, but the displacement is rotated about ninety degrees from the displacement provided by the arrangement of FIGS. 5 and 6 (compare the position of region 24 in FIG. 10 with the position of region 23 in FIG. 6). These Figures are equivalent to FIGS. 1 and 2 having three of the variable reflective termination devices 15 set the same to provide the same phase to three of the feed points 22 and one of the variable reflective termination devices set differently to provide a different phase to the fourth feed point. For example, one of the variable reflective termination device 15 of FIGS. 1 and 2 can be adjusted to provide a short circuit at the connected feed point 22 and the remaining termination devices all set to provide an open circuit to the remaining feed points 22. The comparison of the location of the heating region as steered by the arrangement of FIGS. 9 and 10 and FIGS. 5 and 6 show that with the arrangement of FIGS. 1 and 2 where three of the variable reflective termination devices provide open circuit terminations and one of the variable reflective termination devices provides a short circuit termination, the heating region is displaced away from the short circuit termination. Thus, with the arrangement of FIGS. 1 and 2, the heating region can be steered into one of four offset positions depending upon which of the four variable reflective termination devices is set to provide a short circuit termination while the other three variable reflective termination devices are set to provide open circuit terminations.

FIGS. 7 and 8 are the same as described in the details of FIGS. 1 and 2, but with only two of the adjacent variable reflective termination devices 15 of FIGS. 1 and 2. In this arrangement, equal phase is provided at the two adjacent feed points 22 without the variable reflective termination devices. The adjacent feed points 22 connected to the variable reflective termination devices 15 can be adjusted to provide different phases. This provides steering to displace the heating region. If both variable reflective termination devices 15 in FIGS. 7 and 8 are adjusted to provide a different phase than that provided to the feed points without the variable reflective termination devices to both feed points to which they are connected, the heating region 25, FIG. 8, is displaced from both applicators having the variable reflective termination devices 15 coupled thereto. This provides a displaced heating region 25 in body 18 that is rotated approximately forty five degrees in orientation from the position shown in FIG. 6. FIGS. 7 and 8 are equivalent to FIGS. 1 and 2 having two adjacent variable reflective termination devices set the same to provide the same phase to two of the adjacent feed points 22 and the other two adjacent variable reflective termination devices set differently to provide a different phase or different phases to the other two adjacent feed points. For example, two adjacent variable reflective termination devices can be set to provide an equivalent open circuit at the connected feed points 22 and the remaining two adjacent variable reflective termination devices can be set to provide an equivalent short circuit to the remaining two adjacent feed points 22. This arrangement would provide the same displaced heating region 25 in body 18 shown in FIG. 8 that is rotated approximately forty five degrees in orientation from that shown in FIG. 6. The particular adjacent pairs of applicators in the system of FIGS. 1 and 2 provided with the open circuit terminations and those provided with the short circuit terminations determine in which of four directions the heating region is displaced or offset.

It should be realized that with the arrangement of FIGS. 7 and 8, if one of the variable reflective termination devices 15 shown is adjusted to provide a termination at its connection point the same as at the connection points without the variable reflective termination devices (three connection points provide the same phase signals) and only one of the variable reflective termination devices is adjusted to provide a different termination and thus provide a different phase signal at that one connection point, the system of FIGS. 7 and 8 become equivalent to the system of either FIGS. 5 and 6 or FIGS. 9 and 10. Therefore, if only one of the variable reflective termination devices 15 shown, for example, the variable reflective termination device 15 at the top right in FIG. 8, is set to provide a different phase, e.g., that variable reflective termination device is set to provide a short circuit at its connection point 22, while the other variable reflective termination device and the two connection points without variable reflective termination devices provide open circuit terminations, the apparatus of FIGS. 7 and 8 become equivalent to the apparatus of FIGS. 5 and 6 and the deflection of the heating region is as shown in FIG. 6. Similarly, if the variable reflective termination device 15 shown in the lower left hand portion of FIG. 8 is set to provide a different phase, e.g., that variable reflective termination device is set to provide a short circuit at its connection point 22 while the other variable reflective termination device and the two connection points without variable reflective termination devices provide open circuit terminations, the apparatus of FIGS. 7 and 8 become equivalent to the apparatus of FIGS. 9 and 10 and the deflection of the heating region is as shown in FIG. 10. Further, if both variable reflective termination devices are set to provide the same termination and same phase signal as the two connections without the variable reflective termination devices so that all applicator connections provide open circuit terminations, the system of FIGS. 7 and 8 becomes equivalent to the system of FIGS. 3 and 4 with the heating region centered in the target body. Thus, with the apparatus of FIGS. 7 and 8, variable steering is provided by varying the condition of the variable reflective termination devices. If both of the variable reflective termination devices provide the same phase terminations as the two applicators without the variable reflective termination devices (all four applicators have the same phase signals) the heating region is steered to the center of the target body as shown in FIG. 4. If one or the other or both of the variable reflective termination devices provides a different phase termination at its connection point from the phase provided by the two applicators not connected to variable reflective termination devices, the heating region can be easily steered to the position shown in FIG. 6, the position shown in FIG. 10, or the position shown in FIG. 8.

With the arrangement of two variable reflective termination devices as shown in FIGS. 7 and 8, and by locating the target body in a particular rotated position within the housing 20, the heated region produced by the system can be selectively positioned within the body as desired. In order to position the heated region in the body without rotational movement of the target body in the housing with respect to the two variable reflective termination devices as described, the system of FIGS. 1 and 2 with all four connection points being coupled to variable reflective termination devices is preferred. This arrangement of FIGS. 1 and 2 allows any one or more of the variable reflective termination devices to be set to provide any arrangement of terminations to steer or position the heated region produced by the system at any selected position around the target body. By proper selection of open circuit and short circuit reflective terminations provided by selected variable reflective termination devices around the body, the system can be made equivalent to any of the systems of the remaining figures to provide a central heating region or displaced heating region positioned at any selected rotated position at forty-five degree intervals around the body as described above. If the variable reflective termination devices can provide a wider range of terminations than merely open circuits and short circuits, additional steering of the heating region can be obtained. However, the simple open and short circuit connections provide a system that is simple to operate and provides a good selection of steered heating regions.

FIGS. 11 and 12 are diagrams similar to FIGS. 5 and 6, but show the use of a parasitic applicator which reflects EMR energy back to the target. The parasitic applicator is not connected to the splitter 11 or EMR source 10, however, it is connected to a variable reflective termination device 15. The approximate position of the resulting heating pattern 26 from this arrangement with a single applicator that contains parasitic antennas is shown in FIG. 12 and is similar to that produced by the connection pattern of FIGS. 5 and 6.

FIGS. 13 and 14 are diagrams similar to FIGS. 7 and 8, but showing the use of two adjacent parasitic applicators which reflect EMR energy back to the target. The parasitic applicators are not connected to the power splitter or the EMR source 10, however, they are each connected to a variable reflective termination device 15. The approximate position of the resulting heating pattern 27 from this arrangement with two adjacent applicators each containing parasitic antennae is shown in FIG. 14 and is similar to that produced by the connection pattern of FIG. 8.

FIGS. 15 and 16 are diagrams similar to FIGS. 11 and 12, showing the use of a parasitic applicator which reflects EMR energy back to the target. The parasitic applicator is not connected to the splitter 11 or EMR source 10, however, it is connected to a variable reflective termination device 15. However, the parasitic applicator with coupled variable reflective termination device 15 in FIGS. 15 and 16 is at a different location than in FIGS. 11 and 12. The approximate position of the resulting heating pattern 28 from this arrangement with a single applicator that contains parasitic antennas is shown in FIG. 16 and is similar to that produced by the connection pattern of both FIGS. 11 and 12 and FIGS. 9 and 10.

FIGS. 11 to 16 show that it is not necessary to have a direct connection of all applicators to the power source. Parasitic applicators will reflect EMR energy and can provide steering capability to the system. A minimum system with parasitic applicators to provide phase array steering would be one primary applicator and one parasitic applicator with the parasitic applicator having a variable reflective termination device to adjust the phase of the reflected radiation from the parasitic applicator. Above that, any selected number of primary and parasitic applicators could be used. In addition, combinations of primary and parasitic applicators could be used. An example of such a combination would be a single primary dipole or monopole antenna device that has reflective parasitic antennas to each side of the driven or primary antenna where the side antennas would act as parasitic reflectors based upon their termination. This could even be single dipoles or monopoles having metal strip reflectors to the two sides to form the actual antenna set and the feed point of the dipole or monopole type antenna could have the variable reflective termination device.

FIG. 17 shows an arrangement of the invention where the applicator comprises two cylindrical metal rings 14 which extend around the housing 20 to enclose the target and a bolus containing a dielectric fluid, such as water, between the target and the housing walls. A four channel feed system for coupling EMR power to the applicator provides four energy supply connection points 22 spaced at ninety degree intervals around the rings to provide a balanced feed to the rings. The rings form a single dipole ring applicator. The energy supply connection points 22 are shown as coaxial cables 12 connected to respective rings. Variable phase termination devices 15 for some or all of the energy supply connection points 22 enable the same heating pattern steering that has been shown by the other figures. The connections of the variable reflective termination devices can be placed at each of the energy supply connection points and connected to the coaxial cable connections, as shown, can be connected to some of the energy supply connection points, or can be connected to respective rings between the energy supply connection points at other positions around the applicator. Further, more than four variable reflective termination devices could be used. The termination devices could include coaxial cables connected to the respective rings 14 or to the coaxial cables 12 at the energy supply connection points 22, direct connections between the respective rings, or could be inserts inserted into the space between the respective rings to create short circuits or other terminations.

While the two cylindrical metal rings of FIG. 17 may be considered or referred to as forming a single applicator, since the radiation provided or reflected from different locations around the circumference of the rings can vary and can be controlled, for purposes of the invention, such an applicator is considered as a plurality of applicators.

It should be realized that with any of the applicators, various termination means can be used as the variable reflective termination devices. These can be manually operated devices to provide short circuit, open circuit, or other connections, such as manually operated mechanical switches or lengths of coaxial cable manually connected to a coaxial cable connector at the feed points, or can be remotely controlled terminations such as controlled by electric coaxial relays, PIN diode termination switches, or other remotely controlled switches or devices. Further, the termination can be adjusted by using variable capacitance or other devices, or can be adjusted by adjusting cable lengths coupling a reflective termination device to the feed point. All of these as well as other means of creating reflective terminations at the energy supply connection points or other termination points are considered as variable reflective termination devices within the scope of the invention.

The electromagnetic radiation used with the invention should be in the form of radio frequency and microwave energy in order to create the desired heating regions in the target body.

The applicators can use various antenna configurations such as dipoles, folded dipoles, monopoles, waveguides, parallel strip horns, microcircuit patch antennas, two concentric metal cylinders, etc. These antenna radiators provide a dominant linear polarization and are suitable for providing the deep heating that would be centralized when such deep heating is desired. Circularly polarized antennae such as spiral antenna radiators can also be used. However, circular polarization would not provide as much central heating from an array as a result of the overlapping EMR fields when more than two are used. This is because the dominant fields of spirals that are overlapping from varying directions will not be co-aligned. It is still possible to use such spiral antennas with variable reflective terminations and as parasitic antenna, but the effects on the heating pattern from such will be different than for the linearly polarized antenna arrays.

While the arrangements of the embodiments of FIGS. 5-16 can be used for systems which provide limited steering as described for each embodiment, the embodiment of FIGS. 1 and 2 provides a full range of steering capability and is thus the preferred system to provide maximum steering capability and flexibility to a user of the system. However, while the embodiment of FIGS. 1 and 2 shows all applicators directly coupled to the EMR energy source, this direct coupling is not necessary for the full range of steering and flexibility. A system with the full range of steering can include parasitic applicators or combinations of primary and parasitic applicators. The important thing to get the full range of steering is to provide a variable reflective termination device coupled to each applicator in the system.

In another embodiment, a simplified hyperthermia system having an array of electromagnetic radiation applicators 14 can be integrated with a magnetic resonance imaging (MRI) system and, more particularly, with the MRI system's electromagnetic radiation (EMR) source 91, as illustrated in FIG. 18. The EMR source of the MRI system can be used as the power source for a hyperthermia system using a phased array or other types of radiators, as previously described.

In one embodiment, the MRI system's EMR source 91 can be used to supply an electromagnetic signal to the hyperthermia system applicators 14 by implementing a switching mechanism 99. The EMR source can be an output power amplifier of a magnetic resonance imaging system that is typically used to supply high power EMR signals to an MRI system for imaging purposes. Switching the EMR source between use with the MRI scanner and the hyperthermia system applicators can be accomplished by a number of different means. For example, a coaxial relay can be used to switch the EMR source, PIN diode type switching can be used, or another high power radio frequency means of switching can be incorporated.

The MRI system can be used to form a temperature image. A user can determine temperature changes caused by the hyperthermia system by taking a plurality of temperature images with the MRI system. An MR temperature image may be taken on a periodic basis, such as every ten minutes. It typically takes approximately one minute to obtain the MR image. Thus, when using the hyperthermia system and the MRI system together, the EMR source 91 can be connected to the hyperthermia system applicators 14 a majority of the time.

A typical MRI system includes a receiver configured to detect relatively small signals from the specimen that is scanned, typically a person. Due to the sensitive nature of components within the receive path, such as the preamplifier, the receive path is typically protected when energy is emitted from the MRI system. The same type of protection may be applied when energy is emitted from the hyperthermia system applicators 14. Disabling the MR receive path from an MRI system body coil or other type of MR coil can be accomplished using high power PIN diodes to either short circuit or open the conductive path to the preamplifier. Most MRI system's are already configured to disable the MR receive path when energy is emitted from the coil.

In one embodiment, the MRI EMR source 91 can be configured to output an EMR signal having the same frequency to both the MRI body coil and the hyperthermia system applicators 14. When the output is the same frequency, the MR receive path can be disabled whenever the EMR signal is coupled to either the body coil or the applicators to protect the sensitive receive path devices such as the preamplifier from being damaged by the relatively high energy output from the coil and applicators.

In another embodiment, the MRI EMR source 91 can be configured to output a different frequency to the hyperthermia system applicators 14. For example, the MRI EMR source is typically configured to output an EMR signal at a frequency of approximately 63.5 MHz for a 1.5T system and 127 MHz signal for a 3T system, as previously discussed. When the MRI EMR source is switched to output a signal to the hyperthermia system applicators 14, the EMR signal can be set at a different frequency, such as 100 MHz. Using a different frequency for the hyperthermia system applicators can enable passive filtering to protect the MR receive path. The use of passive filtering, such as band pass, band stop, high pass, and low pass filters can enable the hyperthermia system to be powered with the EMR signal without the need to disable the MR receive path. The passive filtering can be used to substantially filter and thereby block the hyperthermia signal frequency from the sensitive receive path devices, such as the preamplifier.

When the MRI EMR source 91 is connected to the hyperthermia system applicators 14 the signal path can begin at the MRI EMR source, through a transmission means such as a coaxial cable 98, strip line, or other transmission means, into the switch 99, through another transmission line 73, and into the splitter 11. The MRI EMR source may include a signal generator, power amplifiers, and filters used to provide a substantially noise free signal at a desired frequency. The signal can then be passively spilt at the splitter 11 and directed through transmission line 12 to the central energy supply connection points or feed points 22 of each applicator 14. At these feed points 22, there are additional coaxial cables 16 that are used to attach to variable reflective termination devices 15. These variable reflective termination devices control the effective termination seen at the central energy supply connection points 22 to control the phase at each of the applicators, thereby enabling the heating location within the MRI system to be controlled, as previously discussed.

In another embodiment illustrated in FIG. 19, a coupling device such as a capacitive dipole dual coupling ring 97 can be used to couple the EMR signal in the body coil 94 (FIG. 20) of the MRI system to the coupling ring. The coupling ring can be tuned using standard tuning devices such as capacitors and inductors to enable the coupling ring to be resonant and substantially impedance matched at the operating frequency of the MRI EMR source. The energy coupled from the body coil to the capacitive dipole dual coupling ring can then be directed through transmission line 93*a* to a switching device 90, along transmission line 93*b*, and to the passive splitter 11. The signal can then be passively spilt at the splitter 11 and directed through transmission line 12 to the central energy supply connection points or feed points 22 of each applicator 14. The use of a coupling device such as the capacitive dipole dual coupling ring 97 can eliminate the need for a high power switching device 99 (FIG. 18).

The coupling device can be positioned to be sufficiently close to the body coil within the MRI system to efficiently couple energy from the body coil. The energy can be passively, radiatively, or inductively coupled from the body coil to the coupling device. For capacitive coupling, the spacing between the body coil and the coupling device can be within approximately 5 millimeters to provide for strong capacitive coupling. The actual distance depends on the structure of the body coil. In some MRI systems, the body coil is comprised of relatively long wires. Energy from wires can be radiatively coupled. The rings 97 can act as a radiative coupling device. In one embodiment, the rings can be configured as a secondary bird cage type coil that can be inserted into an MRI system aperture where the body coil is located.

The adult human body, when suspended in a free space environment, will resonate as a dipole conductor when exposed to electric fields that are axially aligned with the body at a frequency range that has a free space wavelength that is approximately twice the length of the body. This was reported by Carl H. Durney and coworkers at the University of Utah on a published contract to the United States Air Force in February 1978 on contract report number SAM-TR-78-22. On pages 80 and 81 of this study, it was shown that a typical adult male has a body resonance at a frequency of about 70 MHz and a typical female is resonant at a frequency of about 80 MHz. These results have been used to modify the safety standards for exposure to such fields. In this report, it was shown that the total body absorption of the EMR power in an aligned free-space field at a resonant frequency has an intensity that is five to ten times that of either cross polarized fields or fields at much higher frequency. In this mode, the body acts as a resonant dipole. The resonance occurs over a rather broad frequency range. Such body resonance creates the strongest electrical currents along the central regions of the body, with decreasing current for heating at the ends of the body.

If one end of the body is touching or close to an effective ground plane such as the side zone of an MRI scanner, the body resonant behavior can change to be more like a monopole over the ground plane, changing the resonant frequency to one fourth of a free space wavelength. This results in a quarter wave monopole body resonance for a typical adult male of 35 MHz and 40 MHz for a typical adult female.

In order to substantially reduce the amount of whole body heating and to better focus the EMR emitted from the hyperthermia system applicators 14, a bolus containing a high dielectric material can be used. In one embodiment, the EMR signal directed to the feed points 22 can be radiated from each applicator 14 into a bolus located in the area 19 between the target body 18 and the dielectric shell 20 (FIG. 16) of the MRI (FIG. 16). The bolus can be filled with a high dielectric material such as deionized water. The bolus can enable efficient transmission into a human body since the body has a similar dielectric constant as deionized water. The water can act like a dielectric waveguide for the energy transmitted from the applicators in a similar fashion to light being guided through fiber-optic cables. The use of a water filled bolus closely connected to the hyperthermia system applicators 14 enables the energy to be targeted to the tissue region that is intended without exposing the whole body to the high level stray electric and magnetic fields that can occur without the use of a water bolus.

The bolus can also be useful in cooling of both the whole body and the surface of the body to keep the skin cool in the presence of the energy being directed into deeper tissues. Additionally, presence of the water filled bolus against the body surface has an additional positive benefit that it helps to reduce localization of energy near the surface that can result in superficial hot-spots resulting from anatomical structures such as the lower dielectric tissues of fat and bone that are near the surface.

The displacement currents that are caused to flow in the body by the electric field emitted from the hyperthermia system applicators 14 tend to follow the relatively high conductivity and high dielectric paths with decreased currents in the low dielectric fat and bone tissues. This phenomenon can result in superficial hot-spots due to localization of currents being displaced by superficial bone and fat structures. The placement of a bolus containing high dielectric water against the surface in these areas provides a high dielectric coupling path for these displacement currents to flow, which reduces the localization and intensification of these currents in such areas. An example of the localization and intensification of currents occurs where the hip bone of the pelvis extends toward the body surface causing a low dielectric barrier to the displacement currents that can result in intensification of currents. The currents can concentrate in the high water tissue over and around the bone. Providing a high dielectric surface path using the water filled bolus substantially reduces the high localization of the currents in the high dielectric muscle tissue overlying the bone protrusion.

In one embodiment, the bolus can have a length that is approximately one wavelength. The wavelength of 100 MHz EMR in water is approximately 33 centimeters (cm). For an adult, a typical bolus can have a length around 30 to 45 cm long. For a child, or when imaging a portion of a body such as the leg, the bolus may have a decreased length, around 20 to 30 cm long. The length can have a range of about 0.5 times to 1.5 times the wavelength of the EMR in the bolus medium. A bolus within this range can provide sufficient coupling of the energy emitted from the hyperthermia system applicators 14 to the body. The use of a water filled bolus provides a substantial advantage over radiating into an air medium. The bolus effectively acts as a waveguide, allowing the EMR to be directed to a desired area of the body. In contrast, when the EMR is radiated into air, whole body heating typically occurs.

In one embodiment, coupling of the EMR signal from the body coil to the capacitive dipole dual coupling ring 97 can be achieved by emitting a signal from the MRI EMR source 91 (FIG. 18) to the body coil with a phase that can provide a common voltage field polarization and phase so that the electric field provided near a central zone by all elements of the body coil can have approximately the same orientation and phase. This enables the electric fields coupled to the dual coupling ring to be in phase and therefore additive. Providing a substantially in-phase, additive signal to the dual coupling ring can minimize loading of the body coil fields. Loading of the body coil fields can create an opposing phase relationship for the electric field in the central zone of the body coil. It may be necessary in such a case to provide a disconnect method such as a PIN diode switch 90. The PIN diode switch, or another switching means, can be used to disconnect the coupling path from the capacitive dipole dual coupling ring 97 during the MR image transmit mode to avoid image distortions and artifacts due to the presence of the inductive loops of the capacitive dipole dual coupling ring.

FIG. 20 shows the capacitive dipole dual coupling ring 97 described above for FIG. 19 with a representation of a body coil 94. FIG. 21 shows the body coil with the variable reflective termination devices 15 removed for additional clarity. The body coil is used to transmit and receive signals in an MRI system. The body coil is typically a stationary fixed part of a magnetic resonance imaging device. The body coil can be a bird cage type of MR coil. FIG. 20 shows the MRI EMR power source 91 can be used to couple energy from the body coil to the hyperthermia system applicators 14 through the coupling rings 97. The energy of the body coil 94 can be tightly coupled to the coupling rings to minimize excessive stray field leakage from the body coil into the air outside the MRI system. The tight coupling of the energy provides an efficient transfer of the typical MR output power to the coupling device during tissue heating mode.

In one embodiment, the MRI system can include a switch 79 that is used to switch between the transmit and receive modes of the MR system. As previously discussed, the receive path of the MR can be protected during the transmit mode. When the MR system is set in receive mode, the switch 79 can be opened to prevent the body coil 94 or the hyperthermia system applicators 14 from being powered and damaging the sensitive equipment in the MR receive path.

The capacitive dipole dual coupling ring 97 can be formed from a series of dipoles. While a complete ring can be used to couple power from the MR body coil 94, it would likely result in artifacts in the imaging system due to currents being induced from the magnetic field emitted by the MR system. A break 89 in each of the rings can form a dipole system that allows the coupling ring to capacitively couple to the body coil while minimizing artifacts in the imaging system. A typical dipole system can include dipoles that coincide with the position and paths of the body coil in the MR system. The dipole system can allow near field transmit and receive coupling between the body coil and the coupling rings.

The EMR signal sent to a body coil 94 in an MR system is typically phased to minimize standing waves in an electric field, which corresponds to a maximum magnetic field. The EMR signal can be phased to minimize standing waves in the electric field when the EMR from the body coil transmission has 180 degrees of phase difference in the central region of the body to be imaged. In a standing wave, where the electric field is minimized the magnetic field will be maximized. The capacitive dipole dual coupling ring 97 is configured to couple the energy to provide maximum standing waves in the electric field, while minimizing the magnetic field. When the central energy to produce heating is needed, the standing wave pattern radiated can provide the peak voltage region of the standing wave to be in the central region which results in a minima in the magnetic field in that region of the body.

FIG. 22 illustrates a representation of the capacitive dipole dual coupling ring 97 inside of a typical MR body coil 94. It should be noted that there are a variety of ways to form a body coil. The coupling ring can be configured to couple energy from substantially any type of body coil. Some types of body coils include wires 75 that run longitudinally along the long axis of the body coil. These wires can include tuning capacitors that help to provide a long axis electric field orientation. A coupling tuner 95 can be used to tune the dipole dual coupling rings 97 using tuning capacitors, inductors, and the like to be resonant with the body coil. Breaks 89 within the rings are used to minimize artifacts in the imaging system, as previously discussed. Coupling paths between the breaks can be formed. In one embodiment, the coupling path can be a Tee dipole.

FIG. 23 illustrates that the coupling device can include the capacitive dipole dual coupling ring 97 and also include an array of resonant coupling dipoles 96 placed inside the body coil 94. The array of resonant dipoles can be highly coupled and resonant at the body coil frequency. The resonant dipoles can be joined at the opposite ends to the coupling rings 97 to form a common coupling device. The energy that is coupled to the resonant dipoles can be transferred to the central energy supply connection points or feed points 22 of each of the hyperthermia system applicators 14. The resonant coupling dipole devices 96 can be connected to the feed points 22 through an electronically controlled path length such as a high power phase shifter or a PIN diode. The electronically controlled path length can be used to change the boundary conditions of the phased array to steer the heating pattern. Alternatively, short circuits or open terminations along transmission lines can be used to control and steer the energy to provide directional heating capabilities, as previously discussed.

While a single break is illustrated to form resonant dipole couplers 96, multiple breaks may be made in the resonant coupling dipole devices 96. The coupling devices can be positioned to substantially align with the elements of the body coil 94. The length of the elements that make up the dipoles can correspond with and be positioned with the body coil elements. The body coil elements are typically long axis radiating elements. The coupling devices, such as the resonant dipole couplers 96 can be placed in relatively close proximity with the body coil elements to provide a high level of radiative coupling. It should be noted that multiple breaks 89 are shown in each of the rings of the capacitive dipole dual coupling ring 97. Each of the breaks can include a coupling path such as a Tee dipole.

FIG. 24 illustrates an additional embodiment in which the resonant dipole couplers 96 are not joined together by the capacitive coupling rings shown in FIG. 23. However, the resonant dipole couplers 96 can still be used as resonant dipole antennas. The resonant dipole antennas may be shorter than half wave resonance. At this length, inductors and/or capacitors can be used to tune the resonant dipole antennas to enable resonant and impedance matching that provides efficient energy transfer from the body coil 94 through the resonant dipole antennas and into the hyperthermia system applicators 14 to allow for efficient heating at a desired location within a body.

In another embodiment, a method 2500 for irradiating a target with electromagnetic radiation to produce a heated region is disclosed, as depicted in the flow chart of FIG. 25.

The method includes the operation of coupling 2510 electromagnetic radiation from a transmitting body coil located in an inner area of a magnetic resonance imaging (MRI) system to a coupling device. The electromagnetic radiation can be coupled using inductive, capacitive, or radiative coupling. For example, a capacitive dipole dual coupling ring may be used to couple the energy from the transmitting body coil. An additional operation includes directing 2520 the electromagnetic radiation from the coupling device to at least one of a plurality of energy radiator applicators. The electromagnetic radiation can be directed using transmission lines such as coaxial cables, strip lines, and the like. The electromagnetic radiation can be passively divided using a splitter to divide the energy into substantially equal amplitudes having equal phases at one or more of the plurality of energy radiator applicators.

The method 2500 further comprises emitting 2530 a radio frequency heating signal from the at least one of the plurality of energy radiator applicators into a bolus filled with a dielectric fluid and having an open center region configured to receive a body, wherein the bolus is positioned within the inner area of the MRI system and is operable to receive the radio frequency heating signals from the at least one of the plurality of energy radiator applicators and direct the radio frequency heating signals into a section of the body to produce a heated region within the body. In one embodiment, the dielectric fluid can be deionized water.

A phase of the radio frequency heating signal from at least one of the plurality of energy radiator applicators can be adjusted using a variable reflective termination device coupled to the energy supply connection point of the at least one of the plurality of energy radiator applicators. The variable reflective termination device can be adjusted to adjust the phase of the electromagnetic radiation received at the energy supply connection point to provide the radio frequency heating signal with a desired phase relative to radio frequency heating signals from adjacent energy radiator applicators to allow the radio frequency heating signals to be electronically steered to produce the heated region a selected position within the body.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

What is claimed is:

1. A system for irradiating a target with electromagnetic radiation to produce a heated region, comprising:
a coupling device operable to couple electromagnetic radiation from a transmitting body coil located in an inner area of a magnetic resonance imaging (MRI) system, said MRI system including an MRI electromagnetic radiation source coupled to the transmitting body coil to supply radio frequency electromagnetic radiation to the body coil as part of the MRI imaging process;
a plurality of energy radiator applicators having an energy supply connection point electrically connected to the coupling device to receive electromagnetic radiation energy coupled from the transmitting body coil and supplied to the transmitting body coil by the MRI electromagnetic radiation source, with each of the energy radiator applicators operable to emit a radio frequency heating signal; and
a bolus filled with a dielectric fluid and having an open center region configured to receive a body, wherein the bolus is positioned within the inner area of the MRI system and is operable to receive the radio frequency heating signals from the plurality of energy radiator applicators and direct the radio frequency heating signals into a section of the body to produce a heated region within the body.

2. A system as in claim 1, further comprising at least one variable reflective termination device coupled to the energy supply connection point of at least one of the plurality of energy radiator applicators, wherein the variable reflective termination device can be adjusted to adjust a phase of the electromagnetic radiation received at the energy supply connection point to provide the radio frequency heating signal with a desired phase relative to radio frequency heating signals from adjacent energy radiator applicators to allow the radio frequency heating signals to be electronically steered to produce the heated region a selected position within the body.

3. A system as in claim 1, wherein the plurality of energy radiator applicators are each antennas selected from the group consisting of horn type radiators, patch radiators, dipole antennas, folded dipoles, monopoles, waveguides, and two concentric metal cylinders that surround the body to form a single dipole.

4. A system as in claim 1, wherein at least one of the plurality of energy radiator applicators is a parasitic antenna that is not actively powered from the coupling device.

5. A system as in claim 1, wherein the coupling device is operable to couple electromagnetic radiation from the transmitting body coil using at least one coupling process selected from the group consisting of capacitive coupling, inductive coupling and radiative coupling.

6. A system as in claim 1, wherein the coupling device is a capacitive dipole dual coupling ring configured to capacitively couple the electromagnetic radiation from the transmitting body coil.

7. A system as in claim 6, wherein the capacitive dipole dual coupling ring is operable to be tuned to enable the capacitive dipole dual coupling ring to be resonant and substantially impedance matched at an operating frequency of the electromagnetic radiation coupled from the transmitting body coil.

8. A system as in claim 1, wherein the coupling device is positioned to be within a distance of one centimeter from the transmitting body coil of the MRI to provide for strong capacitive coupling.

9. A system as in claim 6, wherein each ring in the capacitive dipole dual coupling ring is divided into at least two sections, with a coupling path formed between each section to minimize artifacts in images produced by the MRI system.

10. A system as in claim 6, further comprising an array of resonant coupling dipoles joined to at least one of the coupling rings in the capacitive dipole dual coupling ring coupling device.

11. A system as in claim 10, wherein an electrical path length between one or more of the resonant coupling dipoles in the array of coupling dipoles, the coupling rings, and the plurality of energy radiator applicators is adjustable using one of electrical and mechanical means to adjust the electrical path length.

12. A system as in claim 10, wherein a length of elements in the array of resonant coupling dipoles are selected to correspond with and be positioned adjacent radiative elements in the transmitting body coil in the MRI.

13. A system as in claim 1, wherein the coupling device is operable to be slidably inserted into the inner area of the magnetic resonance imaging system.

14. A system as in claim 1, wherein the dielectric fluid is deionized water.

15. A system as in claim 1, wherein the bolus has a length within a range of 0.5 times to 1.5 times a wavelength of the electromagnetic radiation in the dielectric fluid.

16. A system as in claim 1, wherein the bolus is in direct contact with exposed skin on the body to provide an electrical path for currents induced in the body to exit through the bolus in order to reduce localized heating and surface heating of the body.

17. A system for irradiating a target with electromagnetic radiation to produce a heated region, comprising:
    a coupling device operable to couple electromagnetic radiation from an electromagnetic radiation source of a magnetic resonance imaging (MRI) system having an inner area operable to receive a body;
    a plurality of energy radiator applicators having an energy supply connection point electrically connected to the coupling device to receive electromagnetic radiation energy supplied by the electromagnetic radiation source of the MRI system from the coupling device, with each of the energy radiator applicators operable to emit a radio frequency heating signal using the electromagnetic radiation energy from the coupling device;
    a bolus filled with a dielectric fluid and having an open center region configured to receive the body, wherein the bolus is positioned within the inner area of the MRI system and is operable to receive the radio frequency heating signals from the plurality of energy radiator applicators and direct the radio frequency heating signals into a section of the body to produce a heated region within the body.

18. A system as in claim 17, wherein the coupling device is a switch operable to switch the MRI system's electromagnetic radiation source between a body coil located in the MRI system and the energy supply connection point on at least one of the plurality of energy radiator applicators.

19. A system as in claim 18, wherein the MRI system's electromagnetic radiation source is operable to emit electromagnetic radiation at a first frequency when the switch is connected with the body coil in the MRI system and a second frequency when the switch is connected with the energy supply connection point on the at least one of the plurality of energy radiator applicators.

20. A system as in claim 17, wherein the coupling device is a capacitive dipole dual coupling ring used to couple electromagnetic radiation from a body coil located in the MRI system.

21. A method for irradiating a target with electromagnetic radiation to produce a heated region, comprising:
    coupling electromagnetic radiation from a magnetic resonance imaging (MRI) system MRI electromagnetic radiation source to a transmitting body coil of the MRI system, such electromagnetic radiation being usable for producing a radio frequency heating signal;
    coupling electromagnetic radiation from the transmitting body coil located in an inner area of the MRI system to a coupling device;
    directing the electromagnetic radiation from the coupling device to at least one of a plurality of energy radiator applicators; and
    emitting a radio frequency heating signal from the at least one of the plurality of energy radiator applicators into a bolus filled with a dielectric fluid and having an open center region configured to receive a body, wherein the bolus is positioned within the inner area of the MRI system and is operable to receive the radio frequency heating signals from the at least one of the plurality of energy radiator applicators and direct the radio frequency heating signals into a section of the body to produce a heated region within the body.

22. A method as in claim 21, further comprising emitting a radio frequency heating signal into a bolus filled with a dielectric fluid, wherein the dielectric fluid is deionized water.

23. A method as in claim 21, further comprising emitting a radio frequency heating signal into a bolus, wherein the bolus has a length within a range of 0.5 times to 1.5 times a wavelength of the radio frequency heating signal in the dielectric fluid.

24. A method as in claim 21, further comprising emitting a radio frequency heating signal into a bolus, wherein the bolus is in direct contact with exposed skin on the body to provide an electrical path for currents induced in the body to exit through the bolus in order to reduce localized heating and surface heating of the body.

25. A method as in claim 21, further comprising adjusting a phase of the radio frequency heating signal from at least one of the plurality of energy radiator applicators using a variable reflective termination device coupled to the energy supply connection point of the at least one of the plurality of energy radiator applicators, wherein the variable reflective termination device can be adjusted to adjust a phase of the electromagnetic radiation received at the energy supply connection point to provide the radio frequency heating signal with a desired phase relative to radio frequency heating signals from adjacent energy radiator applicators to allow the radio frequency heating signals to be electronically steered to produce the heated region a selected position within the body.

26. A system as in claim 1, additionally including a switch between the coupling device and the energy supply connection points of the plurality of energy radiator applicators to connect and disconnect the energy supply connection points of the plurality of energy radiator applicators and the coupling device.

27. A system as in claim 1, additionally including a switch between the MRI electromagnetic radiation source and the transmitting body coil to connect and disconnect the MRI electromagnetic radiation source and the transmitting body coil.

* * * * *